United States Patent [19]
Brauker et al.

[11] Patent Number: 6,156,305
[45] Date of Patent: Dec. 5, 2000

[54] IMPLANTED TUMOR CELLS FOR THE PREVENTION AND TREATMENT OF CANCER

[75] Inventors: James H. Brauker, Lake Villa; Robin Lee Geller, Buffalo Grove; William D. Johnston, Kildeer; Steven A. Levon, Wauconda, all of Ill.; David A. Maryanov, Kenosha, Wis.

[73] Assignee: Baxter International Inc., Deerfield, Ill.

[21] Appl. No.: 08/462,252

[22] Filed: Jun. 5, 1995

Related U.S. Application Data

[63] Continuation-in-part of application No. 08/272,189, Jul. 8, 1994, abandoned.

[51] Int. Cl.⁷ .......................... A61K 48/00; C12N 15/63; C12N 5/10; C12N 15/09
[52] U.S. Cl. .................... 424/93.21; 424/93.2; 435/375; 435/325; 435/366; 514/44
[58] Field of Search .................. 604/305, 50, 892.1, 604/49, 4, 51, 52, 53; 935/62; 424/277.1, 93.4, 93.219, 93.2; 514/44, 2; 435/320.1, 375, 325, 366

[56] References Cited

U.S. PATENT DOCUMENTS

| | | | |
|---|---|---|---|
| 3,093,831 | 6/1963 | Jordan et al. | 3/1 |
| 3,313,289 | 4/1967 | Kapral | 128/1 |
| 3,699,956 | 10/1972 | Kitrilskis et al. | 128/348 |
| 3,967,618 | 7/1976 | Zaffaroni | 128/130 |
| 3,993,072 | 11/1976 | Zaffaroni | 128/263 |
| 4,011,861 | 3/1977 | Enger | 128/2.06 E |
| 4,069,307 | 1/1978 | Higuchi et al. | 424/22 |
| 4,180,560 | 12/1979 | Katz et al. | 424/21 |
| 4,192,308 | 3/1980 | Michaels | 128/260 |
| 4,207,390 | 6/1980 | Oehrlein et al. | 156/227 |
| 4,217,664 | 8/1980 | Faso | 3/1 |
| 4,229,838 | 10/1980 | Mano | 3/1.4 |
| 4,266,999 | 5/1981 | Baier | 156/227 |
| 4,298,002 | 11/1981 | Ronel et al. | 128/260 |
| 4,306,318 | 12/1981 | Mano et al. | 3/1.4 |
| 4,309,776 | 1/1982 | Berguer | 3/1 |
| 4,309,996 | 1/1982 | Theeuwes | 128/260 |
| 4,321,711 | 3/1982 | Mano | 3/1.4 |
| 4,352,883 | 10/1982 | Lim | 435/178 |
| 4,353,888 | 10/1982 | Sefton | 424/25 |
| 4,368,737 | 1/1983 | Ash | 604/175 |
| 4,374,669 | 2/1983 | MacGregor | 75/208 R |
| 4,378,016 | 3/1983 | Loeb | 128/260 |
| 4,391,909 | 7/1983 | Lim | 435/178 |
| 4,413,359 | 11/1983 | Akiyama et al. | 3/1 |
| 4,475,916 | 10/1984 | Himmelstein | 604/890 |
| 4,487,758 | 12/1984 | Goosen et al. | 424/21 |
| 4,505,266 | 3/1985 | Klesius et al. | 604/277 |
| 4,508,113 | 4/1985 | Malaney | 128/132 D |
| 4,542,539 | 9/1985 | Rowe, Jr. et al. | 623/16 |
| 4,553,272 | 11/1985 | Mears | 623/1 |
| 4,557,724 | 12/1985 | Gregonis et al. | 604/49 |
| 4,576,608 | 3/1986 | Homey | 623/11 |
| 4,597,765 | 7/1986 | Klatt | 623/11 |
| 4,601,893 | 7/1986 | Cardinal | 424/15 |
| 4,624,847 | 11/1986 | Ayer et al. | 424/15 |
| 4,657,544 | 4/1987 | Pinchuk | 623/1 |
| 4,664,669 | 5/1987 | Ohyabu et al. | |
| 4,670,286 | 6/1987 | Nyilas et al. | 424/2 |
| 4,673,566 | 6/1987 | Goosen et al. | 424/19 |
| 4,681,582 | 7/1987 | Yamamoto | 604/890 |
| 4,684,524 | 8/1987 | Eckenhoff et al. | 424/469 |
| 4,685,447 | 8/1987 | Iversen et al. | 128/1 R |
| 4,686,098 | 8/1987 | Kopchick et al. | 424/424 |
| 4,687,481 | 8/1987 | Nuwayser | 604/897 |
| 4,689,293 | 8/1987 | Goosen et al. | 435/1 |
| 4,712,553 | 12/1987 | MacGregor | 128/335.5 |
| 4,723,947 | 4/1986 | Konopka | 604/272 |
| 4,743,252 | 5/1988 | Martin, Jr. et al. | 623/1 |
| 4,795,459 | 1/1989 | Jauregui | 623/1 |

(List continued on next page.)

FOREIGN PATENT DOCUMENTS

| | | |
|---|---|---|
| 1196862 | 11/1985 | Canada. |
| 0 127 989 | 12/1984 | European Pat. Off.. |
| 0 188 309 | 7/1986 | European Pat. Off.. |
| 0 213 908 | 3/1987 | European Pat. Off.. |
| 0 232 543 | 8/1987 | European Pat. Off.. |
| 0 259 536 | 3/1988 | European Pat. Off.. |
| 0 277 678 | 8/1988 | European Pat. Off.. |
| 0 359 575 | 3/1990 | European Pat. Off.. |
| 0 370 292 | 5/1990 | European Pat. Off.. |
| 88 13 531.4 | 5/1989 | Germany. |
| 400 6145 A1 | 8/1990 | Germany. |
| 2 185 408A | 7/1989 | United Kingdom. |
| 2117 647 | 10/1993 | United Kingdom. |
| WO 83/03536 | 10/1983 | WIPO. |
| WO 84/01287 | 4/1984 | WIPO. |
| WO 88/03785 | 6/1988 | WIPO. |
| WO 91/00119 | 1/1991 | WIPO. |
| WO 92/07525 | 5/1992 | WIPO. |

OTHER PUBLICATIONS

Marshall, Science, 269: 1050–1055, 1995.
Miller et al., Faseb J., 9:190–199, 1995.
Culver et al., Trends Genetics, 10(5): 174–172, 1994.

(List continued on next page.)

*Primary Examiner*—Karen M. Hauda
*Attorney, Agent, or Firm*—McDonnell, Boehnen, Hulbert & Berghoff

[57] ABSTRACT

A method to prevent or treat cancer in a patient comprising: administering a first set of tumor cells; where at least some of the first tumor cells have at least one tumor antigen corresponding to antigen of the patient's tumor cells; where the tumor cells are contained in an implantable chamber; the chamber defined by a wall including a porous boundary between the patient's immune cells and the contained cells and pervious to subcellular antigenic material; where the boundary prevents contact between patient immune cells and the contained tumor cells, and where the boundary permits subcellular antigenic materials to exit the chamber; and rendering a second set of tumor cells nontumorigenic; where at least some of the second tumor cells have at least one tumor antigen corresponding to antigen of the patient's tumor cells; administering the second tumor cells to the patient without containing them in a chamber.

39 Claims, 7 Drawing Sheets

U.S. PATENT DOCUMENTS

| | | | |
|---|---|---|---|
| 4,798,585 | 1/1989 | Inoue et al. | 604/93 |
| 4,803,168 | 2/1989 | Jarvis, Jr. | 435/240.22 |
| 4,804,381 | 2/1989 | Turine et al. | 623/1 |
| 4,806,355 | 2/1989 | Goosen et al. | 424/424 |
| 4,816,339 | 3/1989 | Tu et al. | 428/421 |
| 4,826,480 | 5/1989 | Diaz et al. | 424/469 |
| 4,832,686 | 5/1989 | Anderson | 604/49 |
| 4,855,141 | 8/1989 | Eckenhoff et al. | 424/423 |
| 4,871,366 | 10/1989 | von Recum et al. | 623/11 |
| 4,877,029 | 10/1989 | Valentini et al. | 128/334 R |
| 4,878,895 | 11/1989 | Klesius et al. | 604/49 |
| 4,878,913 | 11/1989 | Aebischer et al. | 623/12 |
| 4,880,006 | 11/1989 | Albrektsson et al. | 128/630 |
| 4,892,538 | 1/1990 | Aebischer et al. | 604/891.1 |
| 4,911,717 | 3/1990 | Gaskill, III | 623/11 |
| 4,922,926 | 5/1990 | Hirschberg et al. | 128/784 |
| 4,936,317 | 6/1990 | MacGregor | 128/784 |
| 4,937,196 | 6/1990 | Wrasidlo et al. | 435/313 |
| 4,950,483 | 8/1990 | Ksander et al. | 424/422 |
| 4,990,138 | 2/1991 | Bacich et al. | 604/96 |
| 5,002,661 | 3/1991 | Chick et al. | 210/192 |
| 5,011,472 | 4/1991 | Aebischer et al. | 604/50 |
| 5,015,476 | 5/1991 | Cochram et al. | 424/423 |
| 5,024,670 | 6/1991 | Smith et al. | 623/18 |
| 5,077,215 | 12/1991 | McAuslan et al. | 435/240.23 |
| 5,100,392 | 3/1992 | Orth et al. | 604/175 |
| 5,112,614 | 5/1992 | Magruder et al. | 424/422 |
| 5,156,623 | 10/1992 | Hakematsuka et al. | 623/11 |
| 5,201,728 | 4/1993 | Giampapa | 604/891.1 |
| 5,213,574 | 5/1993 | Tucker | 604/93 |
| 5,219,361 | 6/1993 | von Recum et al. | 623/11 |
| 5,262,055 | 11/1993 | Bae et al. | 210/645 |
| 5,324,518 | 6/1994 | Orth et al. | 424/423 |
| 5,344,454 | 9/1994 | Clarke et al. | 623/11 |
| 5,453,278 | 9/1995 | Chan et al. | 424/422 |
| 5,569,462 | 10/1996 | Martinson et al. | 424/424 |
| 5,653,756 | 8/1997 | Clarke et al. | 623/11 |

OTHER PUBLICATIONS

Hodgson, Exp. Opin, Ther. Pat., 5 (5) : 459–468, 1995.

"NIH Report and Recommendations . . . " Dec. 7, 1995, pp. 1–40.

Porgador et al (1992) Canc. Res. 52, 3679–3686.

Vieweg et al (1995) Canc. Invest. 13, 193–201.

Jaffee et al (1995) Sem. Oncol. 22, 81–91.

Vieweg et al (1994) Canc. Res. 54, 1760–1765.

Chang et al., Human Gene Therapy 4: 433–440, 1993.

Gutierrez et al., The Lancet, 339, 1992, pp. 715–721.

Friedmann, Cancer (supp.), 70 (6), 1992, pp. 1810–1816.

Tsai, J. of the Nat. Cancer Institute, 85(7), 1993, 546–53.

Tepper et al., Hum. Gene Therapy, 5, 1994, 153–164.

Biggs et al, Cancer Res., 1965, vol. 25, pp. 1888–1893.

Pardoll et al., Current Opinion in Immunology, 5, 1993 pp. 719–725.

Tai et al, Cancer Immunol Immunother, 15, 1983, 47–53.

Plautz et al, Proc. Natl. Acad. Sci, 90, 1993, pp. 4645–4649.

Algire and Moore (1958), "Passage of Mouse Leukemia Cells Through Pores of Various Sizes in Diffusion Chambers, " *Transplantation Bulletin*, vol. 5, pp. 425–427.

Algire et al. (1954), "Growth of Cells In Vivo in Diffusion Chambers. I. Survival of Homografts in Immunized Mice, " *J. National Cancer Institute*, vol. 15, pp. 493–507.

Algire, G. "Diffusion–Chamber Techniques for Studies of Cellular Immunity, " National Cancer Institute, Public Health Service, Bethesda, Maryland, pp. 663–667.

Amos and Wakefield (1958), "Growth of Mouse Ascites Tumor Cells in Diffusion Chambers. I. Studies of Growth Rate of Cells and of the Rate of Entry of Antibody, " *J. National Cancer Institute*, vol. 21, pp. 657–670.

Capalbo et al. (1964), "Evaluation of the Diffusion Chamber culture Technique for Study of the Morphological and Functional Characteristics of Lymphoid Cells During Antibody Production, " *J. Immunol.*, vol. 92, pp. 243–251.

Dvorak and Waksman (1962), "Primary Immunization of Lymph Node Cells in Millipore Chambers by Exposure to Homograft Antigen, " Department of Pathology & Neurology Research Laboratory, Massachusetts General Hospital, Boston, pp. 1–15.

Prehn et al. (1954), "The Diffusion–Chamber Technique Applied to a Study of the Nature of Homograft Resistance, " *J. National Cancer Institute*, vol. 13, pp. 509–517.

Stutman et al. (1969), "Carcinogen–Induced Tumors of the Thymus. III. Restoration of Neonatally Thymectomized Mice with Thymomas in Cell–Impermeable Chambers, " *J. National Cancer Institute*, vol. 43, pp. 499–508.

Weaver et al. (1995), "The Growth of Cells In Vivoin Diffusion Chambers. II. The Role of Cells in the Destruction of Homografts in Mice, " *J. National Cancer Institute*, vol. 15, pp. 1737–1757.

Maxwell et al., "Regulated Expression of a Diphtheria Toxin A–Chain Gene Transfected into Human Cells: Possible Strategy for Inducing Cancer Cell Suicide, " Cancer Research 46, 4660–4664 (Sep. 1986).

Russell, "Lymphokine Gene Therapy for Cancer, " Immunology Today, vol. 11, No. 6, (1990).

Ostrand–Rosenberg et al., Abstract, Biological Abstracts, vol. 90, (1990).

Fearon et al., "Induction in a Murine Tumor of Immunogenic Tumor Variants by Transfection with a Foreign Gene, " Cancer Research 48, 2975–2980 (Jun. 1988).

Anderson et al., "Inflammatory Response to Implants," *Trans. Am. Soc. Artif. Intern. Organs*, vol. XXXIV, pp. 101–107.

Campbell and von Recum (1989), "Microtopgraphy and Soft Tissue Response," *Journal of Investigative Surgery*, vol. 2, pp. 51–74.

Christenson et al. (1989), "Tissue Reaction to Intrapertioneal Polymer Implants: Species Difference and Effects of Corticaid and Doxorubicin," *Jounral of Biomedical Materials Research*, vol. 23, pp. 705–718.

Colton et al. (1991), "Bioengineering in Development of the Hybrid Artificial Pancreas," *Transactions of the ASME*, vol. 113, pp. 152–170.

Klomp et al. (1983), "Macroporus Hydrogel Membranes for a Hybrid Artificial Pancreas," *Journal of Biomedical Materials Research*, vol. 17, pp. 865–871.

Knighton and Fiegel (1989), "Macrophage–derived Growth Factors in Wound Healing," *Am. Rev. Respir. Dis.*, vol. 140, pp. 1108–1111.

Knighton et al. (1981), "Oxygen Tension Regulates the Expression of Angiogenesis Factor By Macrophages," *Science*, vol. 221, pp. 1283–1285.

Lanza, Robert P. (1982), "Islet Transplanatation With Immunoisolation,"*Diabetes*, vol. 41, pp. 1503–1510.

Menger et al. (1981), "The Influence of Cyclosporine on the Microvasculature of Xenogenic Pancreatic Islet Grafts, "*Transplantation Proceedings*, vol. 10, pp. 187–196.

Miller et al. (1989), "Characterization of Biomedical Polymer Adherent Macrophages: Interlukin 1 Generation and Scanning Electron Microscopy Studies," *Biomaterials*, vol. 10, pp. 202–205.

Rooth et al. (1989), "Prevention of Detrimental Effect of Cyclospin A on Vascular Ingrowth of Transplanted Pancreatic Islets With Verapamil," *Diabetes*, vol. 38(1), pp. 187–196.

Scharp et al. (1984), "Islets Immuno–Isolation: The Use of Hybrid Artifical Organs to Prevent Islet Tissue Rejection, "*World Journal of Surgery*, vol. 8, pp. 221–229.

Schmidt and von Recrum (1991), "Texturing of Polymer Surfaces at the Cellular Level," *Biomaterials*, vol. 12, pp. 385–389.

Woodard and Salthouse, "The Tissue Response to Implants and Its Evaluation by Light Microscopy,"*J. Biomedical Materials Research*, vol. 27, pp. 837–850.

Green et al. (1994), "Fibroblast Response to Microtextured Silicone Surfaces: Texture Orientation into or Out of the Surface," *J. Biomedical Materials Research*, vol. 28, pp. 647–653.

Meyle et al. (1991), "Fibroblast Shape Conformation to Surface Micromorpholgy," *J. Applied Biomaterials*, vol. 2, pp. 273–276.

Wu and von Recum (1992), "Bulk Chemistry Versus Surface Texture and In Vivo Study of Titanium, Hydroxyapatitis, and Silicone,"Fourth World Biomedical Congress, p. 159.

Schmidt and von Recum (1992), "Cellular Metabolic Activity on Microtextured Silicone," Fourth World Biomaterials Congress.

Meyle et al. (1994), "Influence of Surface Microgeometry on Orientation and Anchorage of Fibroblasts," Fourth World Biomedical Congress.

Brauker et al. (1992), "Neovascularization at a Membrane–Tissue Interface id Dependent on Microarchiterture," Fourth world Biomaterials Congress.

Schreuders et al. (1988), "Normal Wound Healing Compared to Healing Within Porous Dacron Implants," *J. Biomedical Materials Research*, vol. 22, pp. 121–135.

Wasfie et al. (1984), "Inhibition of Epithelial Downgrowth on Percutaneous Access Devices in Swine: II," *Trans. Am. Soc. Artif. Intern. Organs*, vol. XXX, pp. 556–560.

Freed et al. (1985), "Long–Term Percutaneous Access Device," *Trans. Am. Soc. Artif. Intern. Organs*, vol. XXXI, pp. 230–232.

Chehroudi et al. (1988), "Effects of a Grooved Epoxy Substratum on Epithelial Cell Behavior in Vitro and In Vivo," *J. Biomedical Materials Research*, vol. 22, pp. 459–473.

Eskin et al. (1978), "Endothelial Cell Culture on Dacron Fabrics of Different Configurations," *J, Biomedical Materials Research*, vol. 12, pp. 517–524.

Boyce, B. (1982), "A Small Arterial Substitute: Expand Microporous Polytetrafluoroethyelene: Patency Versus Porosity," *Annals of Surgery*, pp. 138–143.

Campbell et al. (19790, "Expanded Microporous Polytetrafluoroethylene as a Vascular Substitute: A Two Year Follow–up" *Surgery*, pp. 177–183.

Squier and Collinms (1981), "The Relationship Between Soft Tissue Attachment, Epithelial Downgrowth and Surface Porosity," *J. Peridontal Research*, vol. 16, pp. 434–440.

PRE-EXISTING DORSAL SQ TUMOR (3 DAYS)

TUMOR RESECTION EXPERIMENTS

IMPLANTED TUMOR CELLS FOR THE PREVENTION AND TREATMENT OF CANCER

This is a continuation-in-part of application Ser. No. 08/272,189, filed on Jul. 8, 1994, now abandoned.

FIELD OF THE INVENTION

This invention relates to cancer prevention and treatment through the implantation of tumor cells into the patient where the tumor cells are contained in a chamber which segregates the tumor cells from the patient's tissues.

BACKGROUND OF THE INVENTION

Currently accepted therapies for most tumors are surgery, chemotherapy, radiation therapy, bone marrow transplants or various combinations of these therapies. In general these treatments are aimed at the destruction of the tumor cells by mechanisms independent of activation of the patient's immune system. In the course of radiation and chemotherapy significant damage to the immune system is an unfortunate side effect. Moreover, the long term effectiveness of these treatments for some tumors is questionable.

a. Activation of the Immune System

Within the last decade therapeutic approaches have been developed based on the activation of the immune system to mediate anti-tumor activity. Generally, a normal host response to tumor cells begins with T-cell recognition of tumor associated antigens on tumor cells or via antigen presenting cells. Recognition via T-cell antigen receptor triggers signal transduction pathways that mediate the activation of the T-cells. This results in secretion of interleukin-2 (IL-2), gamma-interferon, tumor necrosis factor-alpha, and other cytokines from the T-cells and accessory cells. The host immune system is thus mobilized to kill the tumor cells. However, for reasons that are poorly understood, for many tumors this host response does not occur or is inadequate to kill tumor cells.

One therapy designed to activate the immune system is the systemic administration of IL-2. However, the doses of IL-2 required to achieve adequate amplification proved to be toxic to the patient. Cellular immunotherapy approaches to activate the immune system have focused on two types of cells: LAK cells and TIL cells. LAK (lymphokine activated killer) cells are cells of the immune system which have been non-specifically activated through the use of cytokines such as IL-2 (Lotze et al., Cancer Res. 41, p. 4420–4425 (1981); Grimm et al., J. Exp. Med. 155, p. 1823–1844 (1982)) and/or the use of monoclonal antibodies such as anti-CD3 (Ochoa et al., Cancer Res. 49, p. 693–700 (1989)). These cells can mediate significant anti-tumor activity without the major histocompatibility complex (MHC) related restrictions characteristic of the T-cell receptor of classical cytolytic T-cells (CTL). In one recent study continuous infusion of IL-2 and LAK cells for advanced tumors resulted in responses in 12% of patients with melanoma and 3% of patients with renal cell carcinoma (Lotze, Cell Transplantation 2, p. 33–47 (1993)). While most LAK cells characterized to date consist of activated natural killer (NK) cells (Ortaldo et al., J. Exp. Med. 164, p. 1193–1205 (1986); Ferrini et al., J. Immunol. 138, p. 1297–1302 (1987); Phillips and Lanier, J. Exp. Med 164, p. 814–825 (1986)), LAK cells can also be generated from a subset of T-cells known as γδ T-cells (T-cells which lack the classical αβ subunits of the T-cell receptor and instead express the γδ subunits) (Ochoa et al., Cancer Res. 49, p. 693–700 (1989)). LAK cells can also be generated from isolated CD4+ or CD8+ T-cells which have been cultured in the presence of IL-2 and anti-CD3 monoclonal antibodies (Geller et al., J. Immunol. 146, p. 3280–3288 (1991)). TIL (tumor infiltrating lymphocytes) cells are lymphocytes which have been isolated in vitro from tumors. Like LAK cells, these cells can be expanded by culturing in the presence of cytokines such as IL-2 or IL4, but, unlike LAK cells, these cells are tumor specific. Using TIL cells, a 20–50% response rate has been observed in patients with melanoma (Lotze, Cell Transplantation 2, p. 33–47 (1993)).

b. Enhancing Immunogenicity of Tumors

Other approaches for tumor immunotherapy involve increasing the immunogenicity of tumor cells rather than enhancing the activity of responding lymphocytes. It is believed that many tumor cells lack a degree of immunogenicity required to induce an adequate immune response (Houghton and Lewis, "Cytokine Induced Tumor Immunogenicity," ed. Forni et al., Academic Press, p. 35–54 (1994)).

Generally, stimulator cells (such as tumor cells) activate T-cells by engagement of the T-cell receptor with peptide associated with either Class I or Class II MHC molecules on the stimulator cell. These peptides can either be taken up from the external environment by the stimulator cell, in which case they are processed and presented along with MHC Class II molecules or, they can be peptides produced endogenously by the stimulator cell and then presented with MHC Class I molecules. Presentation of exogenously derived peptides by the stimulator cell is referred to as indirect presentation since the peptides are not being presented on the cell from which they were derived. In the case of direct presentation, peptides are presented on the surface of the cells from which the peptides were derived. FIG. 1 is a schematic diagram showing direct vs. indirect presentation.

In addition to the T-cell receptor and MHC antigens, a number of cell surface antigens have been identified that may play a role in mediating interactions between antigen presenting cells and the responder T-cells. These co-stimulatory molecules include intercellular adhesion molecules (ICAMs), vascular cell adhesion molecule 1 (VCAM-1), lymphocyte function-associated antigen 3 (LFA-3), heat stable antigen (HSA) and CD28 on lymphocytes, and the ligand B7 which must be present on the antigen presenting cell (Pardi et al., Immunol. Today 13, p. 224–230 (1992); Chen et al., Immunol. Today 14, p. 483–486 (1993)). Engagement of the T-cell receptor with the antigen presenting cell in the absence of costimulatory molecules can lead to T-cell anergy and failure of the immune response against the tumor (Gimmi et al., Proc. Natl. Acad. Sci. 90, p. 6586–6590 (1993)).

Unique tumor antigens have been defined for several tumors including the MAGE (van der Bruggen et al., Science 254, p. 1643–1650 (1991)) and MART (Kawakami, Proc. Natl. Acad. Sci. USA 91, p. 3515–3519 (1994); Boon et al., Ann. Rev Immunol. 12, p. 337–365 (1994)) antigens for melanoma and mucins for breast and pancreatic tumors (Finn, J. Cellular Biochem. 17D, p. 92 (1993); Domenech et al., J. Cellular Biochem 17D, p. 108 (1993); Fontenot et al., J. Cellular Biochem. 17D, p. 125 (1993)). See also Brown, J. P. et al., U.S. Pat. No. 5,141,742 (melanoma associated antigen). It has been observed that tumor cells do not efficiently present self-peptides (direct presentation) even when the cells do express MHC antigens, suggesting that there might be a defect/deficiency in another molecule necessary for effective direct presentation of antigen by tumor cells. Many tumor cells have been demonstrated to express low levels of B7. Accordingly, one therapeutic approach is to restore the immunogenicity of the tumor cells by the introduction of the gene for B7 into the patient's tumor cells, thus promoting direct tumor antigen presentation (Chen et al., Cell 71, p. 1093–1102 (1993) and EPO 600591; Chen et al., J. Exp. Med. 179, p. 523–532 (1994); Townsend and Alison, Science 259, p. 368–370 (1993); Baskar et al., Proc. Natl. Acad. Sci. USA 90, p. 5687–5690 (1993)). The introduction of the CD28 ligand B7 to immunogenic lymphoma, mastocytoma, melanoma or sarcoma resulted in increased CTL activity against the wild type tumor and protection against subsequent injection with the wild type tumor (Chen et al., Cell 71, p. 1093–1102 (1993) (melanoma); Chen et al., J. Exp. Med. 179, p. 523–532 (1994) (mastocytoma, fibrosarcoma, lymphoma, melanoma, carcinoma); Townsend and Alison, Science 259, p. 368–370 (1993); Baskar et al., Proc. Natl. Acad. Sci. USA 90, p. 5687–5690 (1993) (sarcoma)). Further, injection of EL4 lymphoma cells expressing B7 resulted in a 60% cure rate in mice with established EL4 derived tumors (Chen et al., J. Exp. Med. 179, p. 523–532 (1994)). Similarly, transfection of murine colon adenosarcoma or fibrosarcoma with genes for murine Class I molecules could mediate the regression of unmodified tumor, although tumors were not completely eliminated (Plautz et al., Proc. Natl. Acad. Sci. USA 90, p. 4645–4649 (1993) (fibrosarcoma, colon carcinoma)). This approach is currently being tested in human clinical trials (Nabel, Proc. Natl. Acad. Sci. USA 90, p. 94–97 (1993) (melanoma)). In both these examples the introduction of the foreign genes enhanced direct, Class I mediated recognition of the tumor cells by the effector cells of the host. The response is tumor specific. Treatment with the genetically modified tumor had no effect on the growth of an unrelated tumor. This response is throught to require direct cell-cell contact. See also Hock et al., Gene Therapy Weekly, p. 22 (Jan. 9, 1995) (murine neuroblastoma cells expressing Class II MHC).

A slightly different approach was taken by Trojan et al. for treatment of glioblastoma. Glioma cells express high levels of insulin-like growth factor I (IGF-1). Treatment of glioma cells with an anti-sense gene for IGF-1 appears to reverse the tumorogenic phenotype rendering the cells immunogenic. In these studies, injection of glioma cells expressing the IGF-1 anti-sense sequence resulted in elimination of pre-existing tumor in all animals treated (Trojan et al., Science 259, p. 94–97 (1993)). Although this response was shown to be mediated by CD8+ T-cells, it is not clear whether they are activated directly by the modified tumor cells or indirectly via antigens picked up by antigen presenting cells or both.

Additional approaches for enhancing the immunogenicity of tumors involve engineering the tumor cells to express cytokine genes such as IL-2, IL-4, IL-6, tumor necrosis factor, interferon-γ or granulocyte macrophage colony stimulating factor (GM-CSF) (Dranoff et al., Proc. Natl. Acad. Sci. USA 90, p. 3539–3543 (1993); Golumbek et al., Science 254, p. 713–716 (1991) (renal cell carcinoma); Gansbacher et al., Cancer Res. 50, p. 7820–7825 (1990); Gansbacher et al., J. Exp. Med. 172, p. 1217–1224 (1990); Bannerji et al., J. Immunol. 152, p. 2324–2332 (1994) (fibrosarcoma); Fearon et al., Cell 60, p. 397–403 (1990) (colon carcinoma); Columbo et al., J. Exp. Med. 173, p. 889–897 (1991) (adenocarcinoma); Haddada et al., Hum. Gene Therapy 4, p. 703–711 (1993) (mastocytoma); Lollini et al., Int. J. Cancer 55, p. 320–329 (1993) (mammary adenocarcinoma); Watanabe et al., Proc. Natl. Acad. Sci. USA 86, p. 9456–9460 (1989) (neuroblastoma); Pardoll, Curr. Opin. Oncol. 4, p. 1124–1129 (1992); Tepper and Mule, Hum. Gene Therapy 5, p. 153–164 (1994); Porgador et al., Cancer Res. 52, p. 3679–3686 (1992) (Lewis lung carcinoma); See also WO 92/05262 Hopkins/University of Texas. Here too, the genetically modified tumor cells are able to stimulate an immune response in situations in which the parent tumor lines are non-immunogenic. Researchers in this area have observed that the immune response extends to destruction of unmodified tumor cells as well as the engineered tumor cells and can, in some cases result in complete regression of pre-existing tumor in experimental animals (Dranoff et al., Proc. Natl. Acad. Sci. USA 90, p. 3539–3543 (1993); Golumbek et al., Science 254, p. 713–716 (1991); Gansbacher et al., Cancer Res. 50, p. 7820–7825 (1990); Gansbacher et al., J. Exp. Med. 172, p. 1217–1224 (1990); Bannerji et al., J. Immunol. 152, p. 2324–2332 (1994) (fibrosarcoma); Fearon et al., Cell 60, p. 397–403 (1990); Columbo et al., J. Exp. Med. 173, p. 889–897 (1991); Haddada et al., Hum. Gene Therapy 4, p. 703–711 (1993); Lollini et al., Int. J. Cancer 55, p. 320–329 (1993); Watanabe et al., Proc. Natl. Acad. Sci. USA 86, p. 9456–9460 (1989); Pardoll, Curr. Opin. Oncol. 4, p. 1124–1129 (1992); Tepper and Mule, Hum. Gene Therapy 5, p. 153–164 (1994); Porgador et al., Cancer Res. 52, p. 3679–3686 (1992); Vieweg et al., Gene Therapy Weekly, p. 20 (Nov. 21, 1994) (prostrate cancer)).

In general these experimental protocols involve immunizing animals one or more times with irradiated tumor cells that have been genetically engineered to express the exogenous gene. Irradiation prevents the cells from dividing but does not diminish their antigenicity. Anti-tumor responses are then tested in one of three ways: (i) the animals are challenged with unmodified tumor cells after the immunization process is complete; (ii) the animals are challenged with unmodified tumor cells during the vaccination process; or (iii) small tumors are established before immunization with modified tumor cells.

The majority of the studies utilizing genetically modified tumor cells have involved the introduction of cytokine genes into various tumors (see Pardoll, Curr. Opin. Oncol. 4, p. 1124–1129 (1992); Tepper and Mule, Hum. Gene Therapy 5, p. 153–164 (1994) for reviews). One of the most effective molecules is GM-CSF (granulocyte macrophage-colony stimulating factor) which augments specific immunity for several tumor types (Dranoff et al., Proc. Natl. Acad. Sci. USA 90, p. 3539–3543 (1993) (B16 melanoma, colon carcinoma, lung carcinoma, fibrosarcoma, renal carcinoma)). GM-CSF is unique in that it may be mediating this anti-tumor effect by stimulating the proliferation and differentiation of dendritic cells which are extremely potent antigen presenting cells capable of presenting antigens to both CD4+ and CD8+ T-cells (Steinman, Ann. Rev. Immunol. 9, p. 271–296 (1991)). Metzinger has recently suggested that the only way the immune system can be activated to respond to tumors is via shed antigens being picked up and presented by professional antigen presenting cells such as dendritic cells (Metzinger, Ann. Rev. Immunol. 12, p. 991–1045 (1994)). Similarly Bannerji et al. have recently suggested that the rejection of IL-2 secreting fibrosarcoma cells is not T-cell mediated although the subsequent systemic immunity is dependent upon the presence of both CD4+ and CD8+ T-cells (Bannerji et al., J. Immunol. 152, p. 2324–2332 (1994)). They hypothesize that the destruction of the modified cells is mediated by NK cells resulting in the release of tumor antigens which can be taken up by antigen presenting cells expressing both Class I and Class II molecules on their cell surface. These cells would then be capable of activating both CD4+ and CD8+ T-cells. A similar model has been discussed by Shoskes and Wood (Shoskes and Wood, Immunol. today 15, p. 32–38 (1994)).

In recent experiments Cohen and co-workers have been able to prolong survival of mice with pre-existing melanoma by injecting the animals with allogeneic fibroblasts which have been transfected with the gene for IL-2 and DNA isolated from melanoma cells (Kim and Cohen, Cancer Res. 54, p. 2531–2535 (1994)). By using allogeneic cells there is no need to irradiate the cells, which could affect cytokine expression. Since the transfected cells are fibroblasts they do not form tumors and since they are allogeneic they readily activate the immune system. However, since they are readily rejected there is no long term stimulation of the immune system. Others have mixed cytokine expressing fibroblasts with irradiated tumor cells and then administered the mixture as a vaccine (WO 93/07906, PCT US92/08999). Still others have coupled nontumorous fibroblast cells to an adjuvant and administered the cells as a tumor vaccine (Eggers, U.S. Pat. No. 5,208,022).

Yet another therapy for prevention and treatment of tumors is immunization with tumor antigens (WO 93/06867 Pardoll, Mulligan). Another vaccine protocol is administration of irradiated tumor cells together with a bacterial adjuvant (Pardoll, 5 Cur. Opin. Immunology, p. 719–725 (1993). Others have irradiated unmodified tumor cells and administered them alone as a vaccine (Dranoff et al., 90 PNAS, p. 3539–3543, FIG. 4A (1993)).

c. Tumor Evolution

Most cancers are believed to be clonal in origin and that new subpopulations arise continuously during evolution of a cancer due to Darwinian selection of genetic variants that have a growth advantage. Some of the genetic variants are characteristic of a particular tumor type and in fact can serve as the basis for classifying the severity of tumor, in other cases the changes are idiotypic, i.e. specific to the individual's own tumor. Mutations giving rise to growth advantage include mutations in growth regulatory genes, changes in morphology, hormone dependence, enzyme patterns, and surface antigens. Some of these changes may allow the abnormal cells to escape either homeostatic controls of the patient or destruction by treatment. Conventional chemotherapies are often effective initially in slowing the progression of disease. However, with time, repeated treatments become less effective, perhaps through evolution of successively less sensitive clones (G. Klein and E. Klein, PNAS USA 74, p. 2121 (1977)). See also Schreiber, H., "Tumor Immunology," Chapter 32 in Fundatmental Immunology W. Paul, ed. (1993).

d. Diffusion Chambers

Diffusion chambers which prevent cell to cell contact have been used for many years to study immunologic mechanisms. Klein et al. have used tumor cells in a diffusion chamber as a model to study the host immune response to tumor cells. They conclude that tumor cells produce soluble factors that promote delayed type hypersensitivity and also stimulate angiogenesis which promotes tumor growth (Tumor Biol., 15, p. 160–165 (1994)).

Stillstrom has implanted tumor cells in diffusion chambers in order to induce immunity in rodents and found that after ten weeks the level of immunity induced by tumor cells in a diffusion chamber deposited subcutaneously for seven days was 10–100 times lower than that achieved with directly inoculated cells. In other experiments he found no significant difference in the immune state of animals inoculated directly and those given diffusion chambers containing tumor cells. He also found that chambers were rejected if left subcutaneously for several weeks (Acta Path. Microbiol. Scand., Sect. B 82, p. 676–686 (1974)).

Biggs and Eiselein used diffusion chambers to show that a certain tumor cell type releases a viral particle which diffuses out of the chamber providing immunity to subsequent challenge with the tumor cells. They also show that very low porosity of the chamber can prevent immunization (Cancer Research, Vol 25, p. 1888–1893 (1965)).

Cochrum et al. U.S. Pat. No. 5,015,476 discloses the use of lymphokines or cytokines as an adjuvant when microencapsulating parasites and implanting them to obtain immunization against parasitic infection.

SUMMARY OF THE INVENTION

Applicants' novel cancer therapy cured 60% of experimental tumor bearing animals. When used for the prevention of cancer the method was 100% effective. No experimental animals developed tumors despite challenge with an injection of $10^6$ tumor cells.

Applicants' invention is a method to prevent or treat cancer in a patient comprising: administering a first set of tumor cells, wherein at least some of said first tumor cells have at least one tumor antigen corresponding to antigen found on the patient's tumor cells, wherein the tumor cells are contained in an implantable chamber, the chamber defined by wall means including a porous boundary means between the patient's immune cells and the contained cells, said boundary means being pervious to subcellular antigenic material, whereby the boundary means prevents contact between patient immune cells and the contained tumor cells, and whereby the boundary means permits subcellular antigenic materials to exit the chamber. The administered tumor cells may be unmodified or the tumor cells may be modified to express and secrete an immunopotentiating molecule (e.g. lymphokines).

Alternatively, instead of tumor cells, the administered cells may be nontransformed somatic cells engineered to express tumor associated antigens or other antigens; and they may be further engineered to express cytokines. The tumor cells may be live or irradiated. The tumor cells may be administered prophylactically to prevent tumors from developing or therapeutically to treat existing tumors or metastases. The tumor cells may be autologus tumor cells administered following surgical removal of a tumor. They may be allogeneic. Or, they may be from a tumor cell line developed from an allogeneic donor. The tumor cells may be administered before, during or after other cancer therapies such as chemotherapy or radiation therapy. They may be administered together with local administration of cytokines using, for example, liposomes.

In accordance with the present invention, administered tumor cells are segregated from the patient's cells using any suitable implantable cell-containing chamber which can retain the tumor cells while allowing subcellular material to pass to and from the chamber. The chamber prevents cell to cell contact between the administered cells and the patient's immune cells. The tumor cells may be implanted at the site of an existing tumor or at a site distant from a tumor.

The present invention further provides a chamber containing tumor cells.

In an alternative embodiment irradiated tumor cells are administered in the chamber, with or without live tumor cells also in the chamber. Preferably, the chamber is such that it allows live tumor cells to survive following implantation for a period longer than they would survive if in contact with cells of the patient's immune system.

In another alternative embodiment the chamber is such that it allows irradiated tumor cells contained in it to survive following implantation for a period longer than they would survive if in contact with cells of the patient's immune system. In other words, the chamber preferably delays or prevents rejection of the contained cells. In a preferred embodiment the chamber is of a type that causes a chronic wound healing inflammation at its surface which acts as an adjuvant to enhance the patient's immune response to the implanted tumor cells.

The present invention further provides a novel cancer therapy comprising (i) the administration of tumor cells in an implantable cell-containing chamber, in combination with (ii) the administration of tumor cells which have been rendered nontumorigenic. The tumor cells which have been rendered nontumorigenic are administered outside the chamber as an inoculation of "free" cells. They are preferably rendered nontumorigenic by irradiation. Alternatively, any method which renders them nontumorigenic may be used. For example, it has been reported that administration of nonirradiated tumor cells in combination with IL-2 renders them nontumorigenic. In accordance with the present invention tumor cells administered outside the chamber may be unmodified or they may be modified to express an immunopotentiating polypeptide. Alternatively, instead of tumor cells, the cells administered outside the chamber may be nontransformed cells engineered to express tumor associated antigens or other antigens, with or without cytokines. They may be autologus or allogeneic. Or, they may be from a cell line developed from autologus or allogeneic cells.

The tumor cells implanted inside the chamber or outside the chamber may be autologus, i.e. taken from an existing tumor of the patient. Alternatively, they may be allogeneic: taken from another individual having tumor cells which have tumor antigens corresponding to those found on the patient's tumor cells. Or they may be from a tumor cell line corresponding to the type of tumor to be treated or prevented in the patient. They may also be nontumor cells engineered to express tumor associated antigens or other antigens, with or without concurrent expression of cytokines.

DETAILED DESCRIPTION OF THE INVENTION

Figure 1:
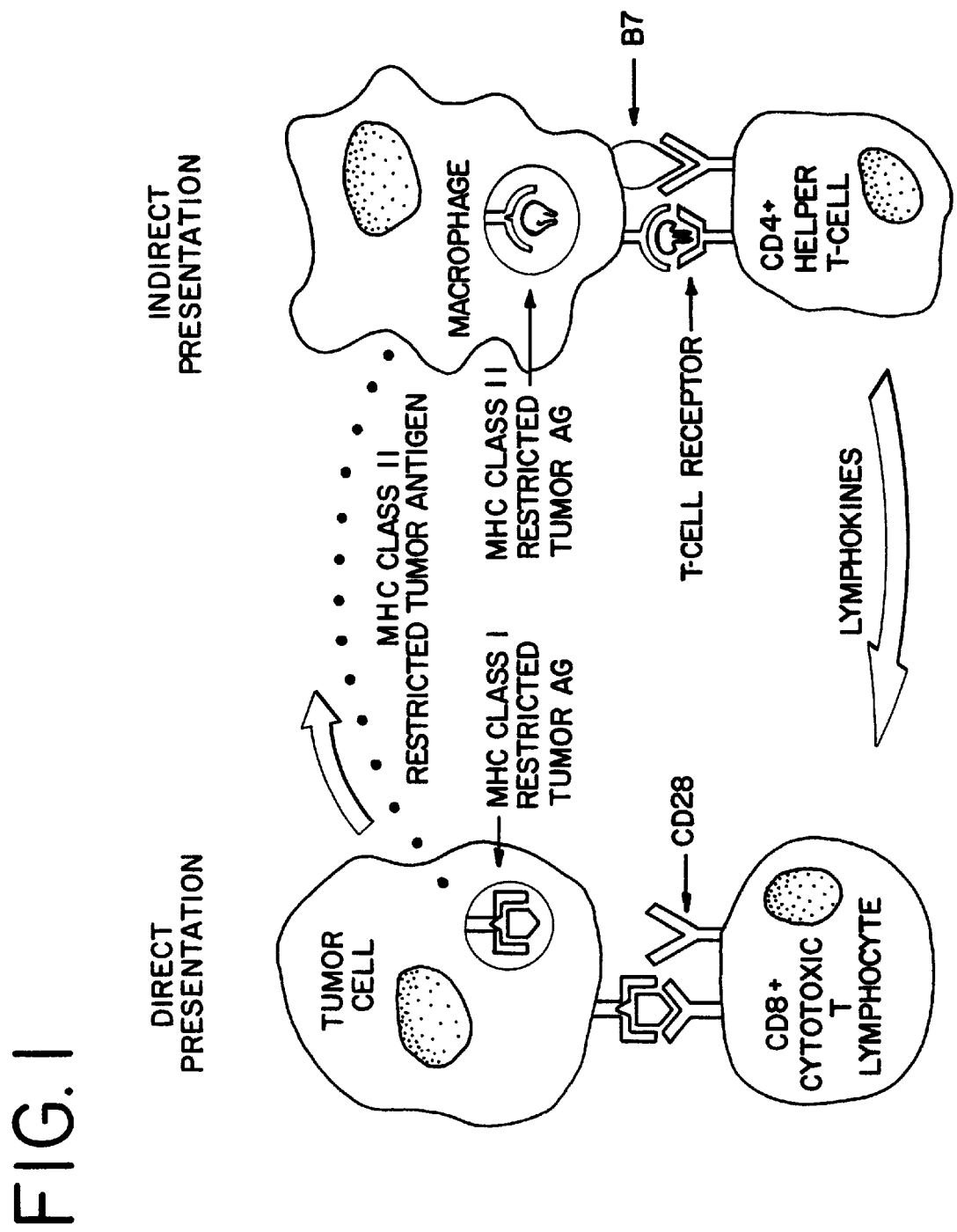
FIG. 1 is a schematic diagram illustrating direct vs. indirect antigen presentation.

A novel method of tumor therapy is described comprising the administration of tumor cells to a patient while preventing cell to cell contact between at least some of the administered tumor cells and the patient's immune cells. As used herein "tumor" shall include solid tumors, metastatic tumor cells and nonsolid cancers of the blood, marrow, and lymphatic systems. "Tumor" shall include: carcinomas (cancers derived from epithelial cells), sarcomas (derived from mesenchymal tissues) lymphomas (solid tumors of lymphoid tissues), and leukemias (marrow or blood borne tumors of lymphocytes or other hematopoietic cells).

As used herein the "treatment" of or "therapy" for cancer shall include applicants' methods which eliminate existing tumor, delay progression of disease, reduce the size of existing tumor, prevent tumor enlargement which would occur without treatment or therapy, delay the onset of tumor formation, delay tumor enlargement, and methods which prevent, reduce or delay metastases. As used herein "metastases" shall mean tumor cells located at sites discontinuous with the original tumor, usually through lymphatic and/or hematogenous spread of tumor cells.

In accordance with the present invention, the tumor cells are implanted in the patient using chamber means that prevents cell to cell contact between the tumor cells and the patient's immune cells. Preferably this segregation is accomplished using a device as described in the published PCT Patent Application WO 92/07525, which is hereby incorporated by reference in its entirety, or the device described in pending U.S. patent application Ser. No. 8/179,860, which is also incorporated by reference in its entirety. Use of a device of this type prevents cell to cell contact, allows subcellular material to pass through the chamber, and provides patient vasculature at the implant site. In addition, it avoids formation of a classic foreign body capsule and it provides a chronic wound healing inflammation at its surface which acts as an adjuvant.

Any device for cellular segregation that allows the implanted tumor cells to interact with the patient's immune system in any way other than through direct cell to cell contact will be suitable. Alternate means include hollow fibers, sheet membranes or encapsulation of single tumor cells or groups of tumor cells in, for example, alginate macro- or micro-capsules or in liposomes. Use of a chamber that can be retrieved intact from the patient is preferred, especially if viable tumor cells are administered in the chamber. This offers the advantage of being able to remove the contained tumor cells from the patient. Use of the preferred chamber also has the advantage of allowing one to administer live autologous tumor cells, live allogeneic tumor cells, or live nontumorous allogeneic or autologous cells engineered to express tumor antigens.

The prior art tumor cell vaccines administered to patients generally use irradiated tumor cells or allogeneic cells without chambers or encapsulation techniques. In accordance with an embodiment of the present invention, nonirradiated living cells contained in the chamber are not rejected or destroyed by the host immune response and are believed to have a continuous immunostimulatory effect for as long as they survive. In contrast, the nonviable tumor cells of the prior art provide only transient stimulation since they are rapidly cleared from the host. The chamber may be implanted in the patient and later loaded with cells or the chamber may be loaded prior to implantation.

Surprisingly, tumor cells administered in the chamber in combination with the administration of free irradiated cells can provide a therapy superior to either technique used separately. Although applicants do not know the mechanism for this result, it is thought that the use of free cells allows early cell to cell contact to initiate an enhanced immune response and the use of cells in a chamber allows a prolonged enhanced immune response thereafter.

In the case of treatment for existing tumor, the administered cells are preferably autologus cells, and preferably comprise a mix of all the various cells which may be present in a heterologus tumor. Preferably the administered tumor cells reflect the heterogenicity of the patient's own tumor. The bulk of the tumor(s) present in the patient are removed using conventional surgical techniques. Removed tumor cells are collected, mixed in a suitable medium, and loaded into a chamber or multiple chambers, depending upon the dose of cells desired. The cells in the chamber may be irradiated or not. The chambers may be implanted subcutaneously, intraperitoneally, at or within the site of the tumor regardless of tissue type, or at any other suitable site. The loaded chamber may or may not be administered in combination with the administration of free nonviable (irradiated) tumor cells at the chamber implant site or distant from the chamber implant site. Multiple chambers and multiple sites may be used.

If allogeneic tumor cells are used they preferably are from a tumor cell line which expresses at least one of the antigens expressed by the patient's tumor as determined by tumor biopsy. The allogeneic cells are administered in the chamber as described herein. The contained cells may be irradiated or not. In addition, the allogeneic cells may be irradiated and also administered as free cells.

Alternatively, in accordance with the present invention, the chamber containing tumor cells may be administered with a dose of immunopotentiating molecules (e.g. lymphokines). The dose may be administered using nontumorous cells (e.g. fibroblasts) engineered to express and secrete immunopotentiating molecules (e.g. lymphokines). The loaded chambers may be administered with or without free irradiated tumor cells, with or without immunopotentiating molecules. The engineered cells may express more than one cytokine or immunopotentiating molecule. Other sources for direct local administration of immunopotentiating molecules may be used such as liposomes, microcapsules, time release capsules, or micro-pumps, all of which are known in the art of drug delivery.

As used herein "immunopotentiating molecule" includes any molecule that stimulates or enhances the activity of the immune system when used in combination with the chamber and tumor cells of the present invention. Those skilled in the art will recognize that this may include cytokines as well as antigenic lipids including phospholipids, hormones, carbohydrates, nucleic acids, virus particle components, bacterial cell antigens, and proteins. Those skilled in the art will recognize that to be of use in the present invention, the immunopotentiating molecule must present in high enough quantities and with a degree of antigenicity adequate to enhance, stimulate or elicit an immune response. The immunopotentiating molecule may be secreted or shed from live or irradiated cells or may be a degradation product from dead cells; or it may be a synthetic or purified drug. Some immunopotentiating molecules are described in Frost et al., WO 92/05262. The use of cytokines as a sophisticated immune adjuvants is known in the art and described by Houghton and Lewis in "Active Specific Immunotherapy in Humans" Chapter 5 of "Cytokine Induced Tumor Immunogenity," Eds. Forni, G. et al. (1994). Golumbek, P. T., et al. describe the co-injection of irradiated tumor cells plus GMC-SF contained in microcapsules, as a cancer vaccine in a murine model (Cancer Research, 53, p. 5841–5844 (Dec. 15, 1993)).

In determining protocols including appropriate doses, one skilled in the art may refer to the many published protocols approved by the National Institutes of Health Recombinant DNA Advisory Committee for cancer vaccines using irradiated modified or unmodified tumor cells. For example, see Human Gene Therapy April 1994 Vol. 5, p. 553–563 and references therein to published protocols. These published protocols include: (i) Immunization of Cancer Patients Using Autologous Cancer Cells Modified by Insertion of the Gene for Tumor Necrosis Factor, Principal Investigator S. A. Rosenberg, Human Gene Therapy 3, p. 57–73 (1992); (ii) Immunization of Cancer Patients Using Autologous Cancer Cells Modified by Insertion of the Gene for Interleukin-2, Principal Investigator S. A. Rosenberg, Human Gene Therapy 3, p. 75–90 (1992); (iii) A Pilot Study of Immunization with Interleukin-2 Secreting Allogeneic HLA-A2 Matched Renal Cell Carcinoma Cells in Patients with Advanced Renal Cell Carcinoma, Principal Investigator B. Gansbacher, Human Gene Therapy 3, p. 691–703 (1992); (iv) Immunization with Interleukin-2 Transfected Melanoma Cells. A Phase I-II Study in Patients with Metastatic Melanoma, Human Gene Therapy 4, p. 323–330 (1993); (v) Gene Therapy of Cancer: A Pilot Study of IL-4 Gene Modified Fibroblasts Admixed with Autologous Tumor to Elicit an Immune Response, Principal Investigators M. T. Lotze and I. Rubin, Human Gene Therapy 5, p. 41–55 (1994) (melanoma, renal cell carcinoma, breast, colon); (vi) A protocol was approved Feb. 17, 1995 for colon cancer which combines tumor cells plus fibroblasts engineered to express IL-2 (San Diego Regional Cancer); (vii) Phase I Study of Cytokine-Gene Modified Autologous Neuroblastoma Cells for Treatment of Relapsed/Refractory Neuroblastoma; Principal Investigator: M. K. Brenner; RAC Approval No. 9206-018; (viii) Phase I Study of Non-replicating Autologous Tumor Cell Injections Using Cells Prepared with or without Granulocyte-Macrophage Colony Stimulating Factor Gene Transduction in Patients with Metastatic Renal Cell Carcinoma; Principal Investigator: J. Simons; RAC Approval No. 9303-040; (ix) Phase I Trial of Human Gamma Interferon-Transduced Autologous Tumor Cells in Patients with Disseminated Maligant Melanoma; Principal Investigator: H. F. Seigler; RAC Application No. 9306-043; (x) Phase I Study of Transfected Cancer Cells Expressing the Interleukin-2 Gene Product in Limited Stage Small Cell Lung Cancer; (xi) Immunization of Malignant Melanoma Patients with Interleukin-2 Secreting Melanoma Cells Expressing Defined Allogeneic Histocompatibility Antigens; Principal Investigator: T. K. Das Gupta; RAC Application No. 9309-056; and (xii) Genetically Engineered Autologous Tumor Vaccines Producing Interleukin-2 for the Treatment of Metastatic Melanomas; Principal Investigator: J. S. Economon; RAC Application No. 9309-058. These protocols are hereby incorporated by reference in their entirety. See also published PCT application WO 93/07906 where a cancer therapy protocol is described for cells expressing IL-2 and PCT Application WO 94/18995 where a protocol for administering allogenic melanoma cells secreting IL-2 (RAC Approval No. 9206-021) is described. One skilled in the art will recognize that the sections therein regarding patient selection, dose, pretreatment evaluation, concurrent therapy, and treatment of potential toxicity are all applicable here. Generally, the desired dose is the number of cells which will be effective to elicit a protective immune response by the patient against the tumor cells. For example, to treat a 70 kg patient having a tumor weighing approximately 150 grams, one would administer approximately $5 \times 10^7$ to $5 \times 10^8$ autologus irradiated or nonirradiated tumor cells contained in a total of 5 to 10 devices having a 40 µl lumen which are described in pending U.S. patent application Ser. No. 8/179,860 filed Jan. 11, 1994, or the number of such devices necessary to contain the desired number of tumor cells. Up to a similar number of free irradiated cells may be administered concurrently. A reduction in the size of tumors present in the patient should be apparent within from about three weeks up to a few months. The elimination of metastases may be harder to detect.

The implant may be left in the patient for a period of weeks for a transient effect. For treatment of existing tumor preferably the implant should remain in the patient for as long as there is a possibility of existing tumor. For prevention of tumors the implant should remain in the patient for so long as the patient continues to be at risk for development of tumors. One or more of the implants may be removed from time to time to assess viability of the implanted tumor cells. Free irradiated cells may be administered at the time of implant and readministered again after a period of time has elaped such that the original free irradiated cells were likely destroyed by the patient's immune system, approximately 2 to 6 weeks. If, as in an embodiment, continued viability of tumor cells is desired, the implant devices may be excised and replaced with new devices containing fresh tumor cells if necessary. Alternatively, the implant may be emptied and reloaded, in place, without excision. The replacement tumor cells may be cells harvested at the time of the original tumor resection and frozen for later use if autologous tumor cells were administered.

In the case of the administration of allogeneic tumor cells similar guidelines will be followed. At least some of the antigens or soluble factors of the donor tumor cells preferably correspond to those found on the patient tumor cells as determined by tumor biopsy.

In accordance with the present invention, where desired, tumor cells may be rendered nontumorgenic by irradiation, by mitomycin C treatment, or other treatments known in the art.

Human cell lines engineered to express known human tumor specific antigens may be created and then administered in accordance with the present invention. Examples of such known tumor antigens include MAGE, MART, and mucins. U.S. Pat. No. 5,141,742 to Brown et al. describes melanoma associated antigens. Again, the antigen(s) of the administered cells preferably correspond, at least in part, with those of the patient's tumor cells as determined by tumor biopsy. The preparation of human cell lines and the engineering of such cells to express desired antigens involve techniques known to those skilled in the art. The cells preferably are of a type which efficiently express the desired antigen or soluble factors. The genetic modification of the cells could be done by one or more techniques well known in the gene therapy field (Human Gene Therapy April 1994, Vol. 5, p. 543–563). One commonly used technique for delivering extrinsic DNA into cells involves the use of retroviral vectors. These vectors can infect large percentages of the target cells and can integrate into the cell genome. The retroviral vectors are constructed to be replication-defective in selected cell lines, and therefore incapable of infecting nontransduced cells. Other viral vectors that have been proposed or used for delivering DNA into cells include adenovirus, adeno-associated virus, herpes virus, and poliovirus. The retroviral and adeno-associated virus vectors are most often proposed or used for ex vivo gene therapy, i.e. DNA delivery into cells removed from the body of the patient.

Non-retroviral delivery techniques that have been used or proposed for gene therapy include DNA-ligand complexes, gene gun techniques and electroporation, and lipofection. Under most conditions, these delivery techniques, as well as certain viral vectors such as adenovirus vectors, do not lead to significant integration of DNA in the cell genome. This means that stable transformations of the recipient cells with the extrinsic DNA occur with very low frequency. Depending upon the particular conditions either viral or nonviral methods would be suitable for the introduction of genes into the cells which are then implanted in accordance with the present invention. Genetic manipulation of primary tumor cells has been described previously (Patel et al., Human Gene Therapy 5, p. 577–584 (1994)).

The applicants' method for prevention of cancer is particularly appropriate for patients at high risk for development of tumors; for example, those individuals identified by genetic screening to be at high risk for development of tumors. As a therapy for patients diagnosed with cancer, applicant's therapy is especially appropriate for patients who have undergone successful tumor resection and patients who are at high risk for the presence of micrometastases.

Figure 2A:
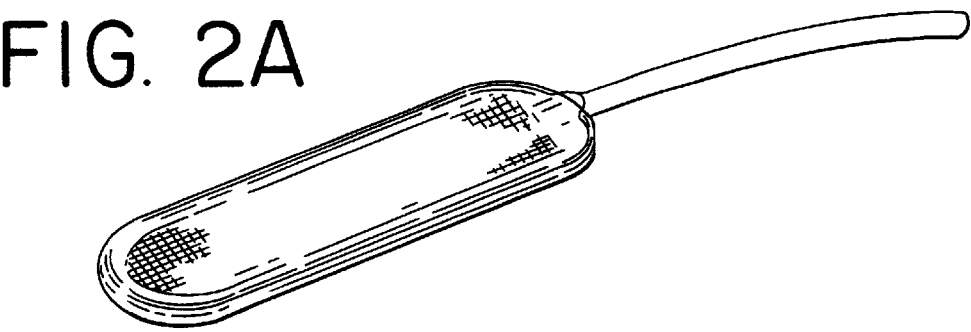
FIG. 2 is a diagram of the chamber used in a preferred embodiment of the invention.
Figure 2B:
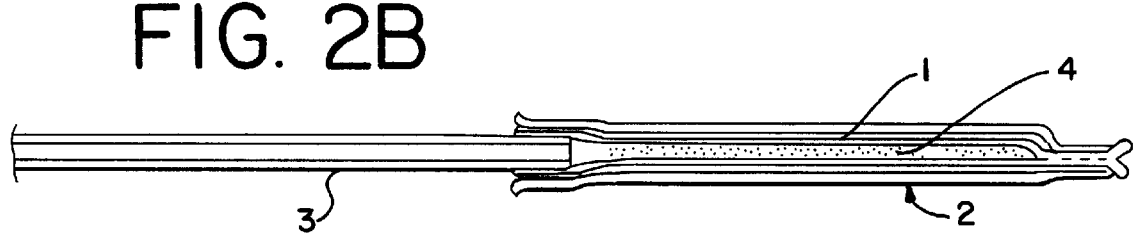

The chamber used in the present invention prevents direct cell to cell contact between the cells of patient's immune system and the cells in the chamber. The preferred chamber of the present invention (FIG. 2) is a device comprising two bilayer membranes (1) surrounded by a polyester mesh (2) sonically welded together, with a port (3) for access to the lumen (4). Each bilayer comprises a 5 µm PTFE membrane manufactured by Gore, Flagstaff, Arizona, Product No. L31324 and a 0.45 µm PTFE membrane manufactured by Millipore, Bedford, Mass., Product No. SF1R848E1. At one end there is a polyester (PE 90 ID 0.034" by OD 0.050") port to permit access to the interior of the device for loading cells. The device has an interior lumen. This device is described in copending application Ser. No. 8/179,860 filed Jan. 11, 1994 and copending application Ser. No. 8/210,068 filed Mar. 17, 1994. Previous studies have shown that this preferred device has the advantage (though not required for all embodiments of the present invention) of being able to protect allograft tissue from immune rejection for extended periods (Carr-Brendel et al., J. Cellular Biochem. 18A, p. 223 (1994) and Johnson et al., Cell Transplantation 3, p. 220 (1994)).

Other cell containing chambers which those skilled in the art may find useful in the present invention include: Agarose microcapsules (Iwata et al., J. Biomed. Mater. Res. 26, p. 967–977 (1992); J. Bioact. and Comp. Polymers 3, p. 356–369 (1988), and Depuy et al., J. Biomed. Mater. Res. 22, p. 1061–1070 (1988)); Hollow fibers of XM50 (Winn et al., J. Biomed. Mater. Res. 23, p. 31–44 (1989) and Altman et al., Proc. of Third Meeting of ISAO, Supp. 5, p. 776–779 (1981); Diabetes, 35, p. 625–633 (1986)); Alginate-polylysine (Wong et al., Biomat., Art. Cells and Immob. Biotech. 19, p. 675–686 (1991)); Microcapsules of alginate-polylysine (O'Shea et al., Biochim. et Biophy. Acta 804, p.133–136 (1984), Sun et al., App. Biochem. and Biotech. 10, p. 87–99 (1984), Chicheportiche et al., Diabetologia 31, p. 54–57 (1988) and Goosen et al., U.S. Pat. No. 4,689,293, Aug. 25, 1987; U.S. Pat. No. 4,487,758, Dec. 11, 1984; U.S. Pat. No. 4,806,355, Feb. 21, 1989, and U.S. Pat. No. 4,673,566, Jun. 16, 1987); Chitosan-alginate (McKnight et al., J. of Bioact. and Comp. Poly. 3, p. 334–355 (1988)); Polyacrylonitrile or other ultrafiltration membranes in a U-shaped device (Moussy et al., Artif. Org. 13, p. 109–115 (1989), Lepeintre et al., Artif. Org. 14, p. 20–27 (1990), and Jaffrin and Reach, U.S. Pat. No. 4,578,191, Mar. 25, 1986); Hollow fibers of polyacrylonitrile (Aebischer et al., Biomat. 12, p. 50–56 (1991) and Lacy et al., Science 254, p. 1782–1784 (1991)); Track-etched polycarbonate membrane diffusion chambers (Gates and Lazarus, Lancet, Dec. 17, p. 1257–1259 (1977)); Polymerized 2-hydroxyethyl methacrylate pHEMA membrane devices (Ronel et al., J. Biomed., Mater., Res, 17, p. 855–864 (1983)); Microcapsules of polyacrylates (Douglas and Sefton, Biotech and Bioeng. 36, p. 653–664 (1990); Trans Am. Soc. Artif. Inter. Org. 35, p. 791–799 (1989)); Acrylic copolymer hollow fibers (Lanza et al., Proc. Natl. Acad. Sci. 88, p. 11100–11104 (1991)); polyol copolymer film WO 93/22427; Intravascular devices (Berguer, U.S. Pat. No. 4,309,776, Jan. 12, 1982) and Gaskill, U.S. Pat. No. 4,911,717, Mar. 27, 1990); Cationic-anionic crosslinked membranes, e.g. chitosan and polyaspartic or polyglutamic acid (Jarvis, U.S. Pat. No. 4,803,168, Feb. 7, 1989); Surface-conforming bonding bridge layer of a multifunctional material and semipermeable polymer layer for cell encapsulation (Cochrum, U.S. Pat. No. 4,696,286, Sep. 29, 1987); Vascular perfusion devices (Chick et al., U.S. Pat. No. 5,002,661, Mar. 26, 1991); Macromer polymer encapsulation, Desai et al. WO 93/16687; Barium-alginate cross-linked microcapsules (Zekorn et al., Acta. Diabetol. 29, p. 99–106 (1992)), other membrane devices (Ward et al., Fourth World Biomat. Con., Berlin, p. 152, Apr. 24–28, 1992)); other encapsulation devices (Aebischer, WO 94/07999; U.S. Pat. No. 5,283,187; WO 93/00128; WO 93/00127; WO 93/00063; WO 92/19195; WO 91/10470; WO 91/10425; WO 90/15637; WO 90/02580) and cellular implant devices: U.S. Pat. Nos. 4,241,187; 4,892,538; and 4,391,909. "Islet Transplantation with Immunoisolation," Lanza, R. P. et al., 41 Diabetes, p. 1503 (1992) reviews various chambers used for containing cells; as do Langer and Vacanti in "Tissue Engineering," 260 Science, p. 920 (1993). In the event that the particular chambers described above are not permeable enough to allow ingress and egress of the subcellular material to and from implanted tumor cells, one skilled in the art will understand that the permeability of such chambers may be altered without changing the basic design of such chambers.

Furthermore, the applicants believe that other devices, not mentioned here, may be used in the invention if they have the property of housing implanted cells in such a way as to prevent direct contact of graft cells and host immune cells, and allow the release of the subcellular antigenic material that stimulates the patient immune response. While applicants have not isolated or characterized the subcellular material which causes the patient immune response, they believe it to include immunogenic molecules (antigens) shed or secreted from the contained tumor cells. The tumor cells shed many antigens, not just tumor associated antigens. This is thought to recruit high numbers of macrophage and antigen presenting cells to the site which in turn provide an enhanced immune response. The administration of an immunopotentiating molecule, such as a cytokine, further enhances the immune response at the site.

Applicant's invention provides numerous advantages over current cancer immunotherapies. Many of the studies published to date require the sole administration of "free" irradiated cells; i.e. cells not contained in a chamber. The cells are irrradiated as a safety precaution to prevent them from proliferating and causing additional tumors. However, they are cleared from the body within 1 to 2 weeks providing only a transient dose, and in some cases, the irradiation may interfere with production of any cytokines engineered into the cells. In applicant's invention it is not always necessary to irradiate the contained cells. Although even when irradiated cells are used they likely remain present as immunogens in the chamber for periods of time longer than the free irradiated cells of the prior art. Applicant's use of a chamber offers the safety of sequestering the tumor cells so that, unlike the prior art, free tumor cells need not be introduced into patients. Moreover, in a preferred embodiment using the preferred chamber, the chamber itself acts as an adjuvant for the subcellular antigen materials. Macrophages are attracted to the outer surface of the device and thus are in a position to pick up antigenic materials as they are shed from the tumor cells within the device.

Examples of engineered cells which may be used in accordance with the present invention include tumor cells engineered to secret cytokines (Sobol et al., WO 95/07105; Addison et al., Gene Therapy Weekly, p. 19 (November 1994)); cells engineered to express foreign antigens to increase the cellular and/or humoral antitumor activity (Plantz et al., PNAS 90, p. 4645 (1993) (allogenic histocompatibility gene); Gansbacher WO 94/18995 (allogenic tumor cell engineered to express cytokines, adhesion molecules, constimulatory factors or tumor associated antigens); Allione et al., Gene Therapy Weekly, p. 20 (January 1995) (mammary adenocarcinoma cells engineered to express IL-2, IL-4, IL-6, IL-7, IL-10, TNF , CMCSF); Hock et al., Gene Therapy Weekly, p. 22 (January 1995) (murine neuroblastoma expressing Class II MHC) (although this approach is thought to require direct cell-cell contact, shed MHC would be an immunopotentiating molecule in accordance with the present invention)); and co-expression in tumor derived cells of both an immunopotentiating molecule and a suicide gene (Frost et al., WO 92/05262).

Overall, the following examples and data presented in the figures demonstrate effectiveness of applicant's invention in a number of different experimental situations. When a chamber containing tumor cells is used as a vaccine (i.e. before tumor formation) it can be effective in preventing tumor formation in as much as 100% of experimental animals. When implanted in the presence of microtumor we demonstrate effectiveness in greater than 75% of the animals tested. Finally, when combined with surgical resection of large tumors, implantation of devices prevented tumor regrowth in 60% of the implanted animals.

Taken together, several conclusions can be drawn from these data. First, when reviewing all the examples, one can conclude that although cure is not achieved in 100% of the animals, it is nevertheless better to have a chamber than not. At worst, the tumors develop more slowly, at best, the animals never develop tumor; in no case do animals develop tumors more quickly or have larger tumors in the presence of a chamber than the control animals. The data further demonstrate that when using the chamber, tumor cells without genetic modification can be used effectively to generate an anti-tumor immune response. Tumor cells in a chamber are much more effective than free tumor cells in generating this immune response and irradiated cells in the chamber appear to be more effective than living cells. It is assumed that this is due to an enhancement of the immunogenicity of the cells due to irradiation induced changes in the cells.

The following examples are provided for illustration of several embodiments of the invention and should not be interpreted as limiting the scope of the invention.

EXAMPLE 1

Rodent Adenocarcinoma Model

Cell lines used: MCA-38 (a generous gift of Dr. Augusto Ochoa, NCI) is a murine colon carcinoma which can be maintained in vivo or in vitro. For in vitro maintenance, the cells were grown in RPMI (Sigma Chemical Company, St. Louis Mo.) supplemented with 1 mM HEPES, 1% non-essential amino acids, 1% L-glutamine, 1% sodium pyruvate, 1% penicillin/streptomycin (Sigma), 0.1% β-mercaptoethanol and 10% fetal bovine serum (Irvine Scientific, Irvine Calif.). Cells were routinely passaged by trypsinization twice a week.

Animals used: For most experiments, female C57/B6 mice (Harlan Sprague Dawley) were used. Where indicated, athymic mice (Harlan Sprague Dawley) were used. All animals were maintained according to standard procedures for care and use of laboratory animals.

Device: These studies utilized sonically sealed 4.5 μl or 20 μl ported devices employing laminated membranes described above and in U.S. patent application Ser. No. 8/179,860. Devices were sterilized overnight in 70% ethanol and then the ethanol was removed by three washes in sterile saline (Baxter Scientific Products, Waukegan Ill.).

Implantation of devices: For loading, MCA-38 cells were trypsinized, washed and pelleted by centrifugation. Except where indicated, MCA-38 cells were encapsulated into 4.5 μl ported devices by loading $10^6$ cells in 3 μl into the central lumen of the device using a Hamilton syringe. The larger device was loaded with $10^7$ cells in 20 μl. Devices were sealed with a silicone plug laid down using a 23 gauge needle and syringe. The device port was completely filled with silicone and the port was cut in half. The remaining port was dipped briefly in 70% ethanol. The loaded devices were washed through three changes of saline. Devices were placed in RPMI 1640 supplemented as described above and incubated at 37° C. until implantation.

The animals receiving implants were anaesthetized by intraperitoneal injection of 0.2–0.3 ml of the mixture of 1 ml ketamine (Fort Dodge Laboratories, Fort Dodge, Iowa) and 0.75 ml xylazine (Rugby Laboratories, Rockville Center, New York) diluted into 1 ml of sterile saline. The abdominal area was swabbed with betadine and a ventral midline incision was made. Using a hemostat a small pocket subcutaneous was made on either side of the midline incision and one 4.5 μl device was inserted into each pocket. Once the devices were inserted the incision was closed using sterile staples and the abdominal area swabbed again with betadine. When using the 20 μl device, only one is inserted.

Tumor challenge: At the indicated times the animals were challenged with an injection of unencapsulated MCA-38 cells. For challenges after implantation, $10^6$ freshly trypsinized MCA-38 cells were diluted in 50 μl of sterile saline and injected into the muscle of the right hind leg. In the case of rechallenge, the second injection of $10^6$ cells was made into the left hind leg and, where applicable, the third injection of $10^6$ cells was made into the right leg. For challenge at the time of implant, animals were challenged with $10^3$ free MCA-38 cells. Preliminary studies have shown that as few as 500 free MCA-38 cells are sufficient for tumor formation.

Histology: Upon completion of each experiment, implanted devices were recovered, fixed in glutaraldehyde, sectioned and analyzed by hematoxylin and eosin staining for the presence of surviving tumor cells within the device using light microscopy.

Survival of MCA-38 cells within immunoisolation devices: To assess the ability of MCA-38 to survive within the device in the absence of immune attack, $10^4$ or $10^6$ cells were encapsulated within 4.5 μl devices and implanted into athymic mice. At the end of the three week implant period, the devices were explanted, processed histologically, and analyzed for the presence of living tissue. MCA-38 cells did survive within the device. In all cases there was a substantial necrotic area in the center of the device but healthy appearing cells were present along the periphery. The width of the necrotic area depended upon the initial number of cells loaded into the device (i.e. greater necrosis in devices containing $10^6$ cells than those containing $10^4$ cells).

Use of devices containing MCA-38 cells as a tumor vaccine: Syngeneic C57/B6 mice were implanted with two devices each containing $10^6$ MCA-38 cells for three or four weeks. These animals were then challenged with an injection of $10^6$ free MCA-38 cells as described above. As shown in Table 1 below 0/8 animals in two experiments developed tumors at the challenge site while all of the control animals developed tumors within ten days of the injection. Empty devices implanted into mice did not protect them against a subsequent challenge with free MCA-38 cells.

Five of these animals received a second challenge of $10^6$ cells 8–11 weeks after the initial implant. In this case 4/5 of the implanted animals remained tumor free at both implant sites; once again all of the control animals developed tumors at the injection site. One experimental animal did develop a tumor at the site of the second injection, this animal was implanted with only one device.

Three of the animals that remained tumor free were given a third challenge seven months after the devices were implanted. For two of the animals the subcutaneous devices were removed before the tumor challenge was given, the third animal was challenged with the devices remaining in place. The animal with the devices remained tumor free after the third challenge while both of the animals from which devices were removed developed tumor as did all the control animals which had never received a device. However, while the animals which had their devices removed did develop tumors, they did so much more slowly than the control animals. Controls developed tumor 10 days after the challenge. One of the experimental animals developed tumor 25 days after the challenge and the second developed tumor 36 days after the challenge. Histology of the removed devices revealed that >90% of the cells were dead and that there was extensive calcification of the material inside of the device. However, there was evidence of a few remaining live cells. These results suggest that the device itself does not mediate the anti-tumor effect since the animals whose devices were removed did not develop tumors at the same rate as controls that had never been implanted with devices. At the same time, the device appears to be necessary to maintain the immunological protection against the tumor; while tumors appear more slowly in animals whose devices are removed, there appears to be no long-term immunity in animals which had been implanted with device in the absence of those devices.

Figure 3:
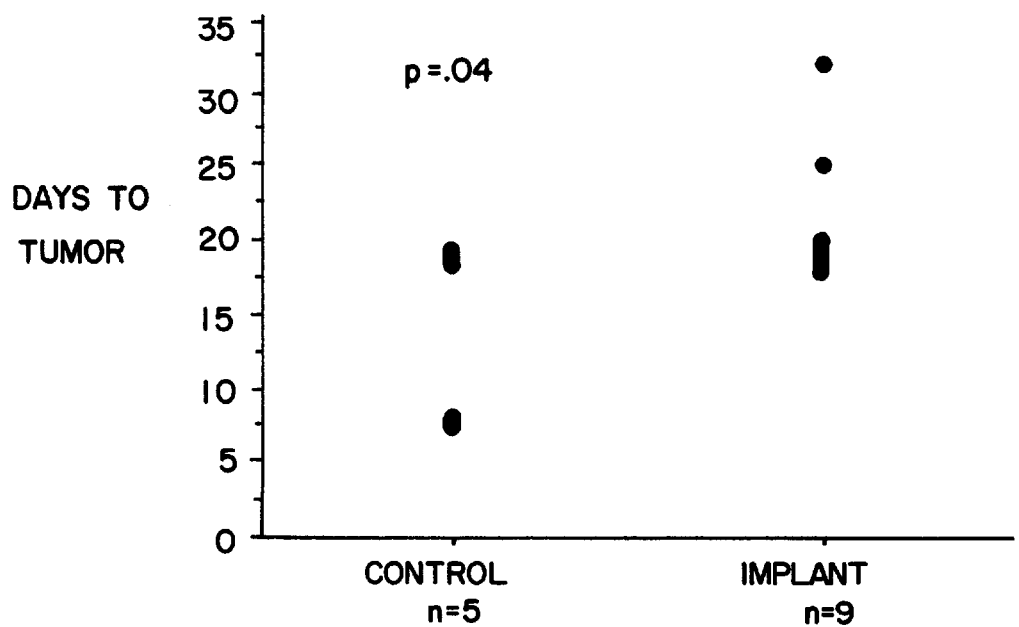
FIG. 3 shows the number of days at which tumor was detected at the challenge site in animals challenged with $10^3$ MCA-38 cells at the time of device implantation, as described in Example 1. Control animals did not receive devices.

Use of devices containing MCA-38 cells as a tumor therapy: In another series of experiments, animals were challenged with free MCA-38 cells at the time of implant of devices containing MCA-38 cells. In this case, the animals were challenged with $10^3$ free tumor cells. In one experiment we were able to significantly delay the time of tumor formation (FIG. 3) p=0.036. In this experiment one animal was tumor free at time of sacrifice at day 32. In a second experiment, all of the animals without devices had developed tumor by day 16 at which time only 1/10 of the implanted animals had developed a tumor at the challenge site. These results suggest that the implantation of a device containing tumor cells can delay or prevent the growth of tumors introduced at the time of implantation.

Table 1 is a table showing the response of mice to tumor challenge following treatment according to the present invention. Animals were implanted with two devices with each containing $10^6$ cells. One animal received only one device. All animals were given the first challenge with $10^6$ free MCA-38 cells three weeks after implant. In Experiment I, a second challenge was at 8 weeks after implant; in Experiment II a second challenge was given at 11 weeks after implant.

TABLE I

RESPONSE OF IMPLANTED MICE TO CHALLENGE WITH FREE MCA-38 CELLS

| Experiment | Implanted with Devices Containing MCA-38 Cells | Tumor Challenge 1 No. mice with tumor/total No. mice | Tumor Challenge 2 No. mice with tumor/total No. mice |
| --- | --- | --- | --- |
| I | + | 0/4 | 1/3 |
|   | − | 4/4 | 4/4 |
| II | + | 0/4 | 0/2 |
|   | − | 4/4 | 4/4 |

EXAMPLE 2

Canine Model

Animals Used: A dog in the Baxter animal facility (142-3) was identified with several subcutaneous masses ranging in size from pinhead to about the size of a quarter. Histological analysis diagnosed these masses as epithelial inclusions cysts. A second dog (4008) was purchased from an outside vendor. This dog had a mammary tumor approximately 10 cm in diameter that was biopsied and diagnosed as an intraductular mammary carcinoma.

Device: These studies utilized the sonically sealed 40 μl ported device employing laminated membranes described above and in U.S. patent application Ser. No. 8/179,860. Devices were sterilized overnight in 70% ethanol and then the ethanol was removed by three washes in sterile saline (Baxter Scientific Products, Waukegan Ill.).

Implantation of Devices: Dogs were anaesthesized by standard methods. The area around the tumors was shaved. In the case of dog 142-3, the largest mass was surgically excised and placed into sterile saline. The mass was cut into small pieces using two pairs of surgical scissors. The minced pieces were loaded into the immunoisolation device as follows: 80 μl of gravity settled tissue was taken up into a Hamilton syringe. The needle of the syringe was inserted into the port of the device and the contents emptied into the lumen of the device. Devices were sealed with a silicone plug laid down using a 23 gauge needle and syringe. The device port was completely filled with silicone and the port was cut in half. Using a hemostat a small pocket was made on either side of the site from which the tumor was explanted and one device was inserted into each pocket (a total of two devices were implanted). Once the devices were inserted the incision was closed and sutured and the abdomenal area swabbed again with betadine.

In the case of dog 4008 ~95% of the tumor mass was surgically excised with cauterization of involved blood vessels. The incision was then sutured and a baseline measurement of the remaining tumor was taken. The excised tumor was cut open and several 0.5 cm diameter pieces removed at various depths. These pieces were further minced using two pairs of surgical scissors. The minced pieces were loaded into eight devices as described above. Four small ventral subcutaneous incisions were made dorsal to the site from which the tumor had been excised and two devices were inserted into each incision. The incisions were then sutured and the abdominal area swabbed with betadine.

Monitoring of animals: The remaining masses in dog 142-3 were measured 2 to 3 times a week. Measurements were taken in two dimensions and used to calculate total surface area of each mass. Duplicate measurements were made by two different technicians and the values were averaged for each time point. Similarly, the tumor remaining in dog 4008 was measured three times a week in two dimensions.

Figure 4:
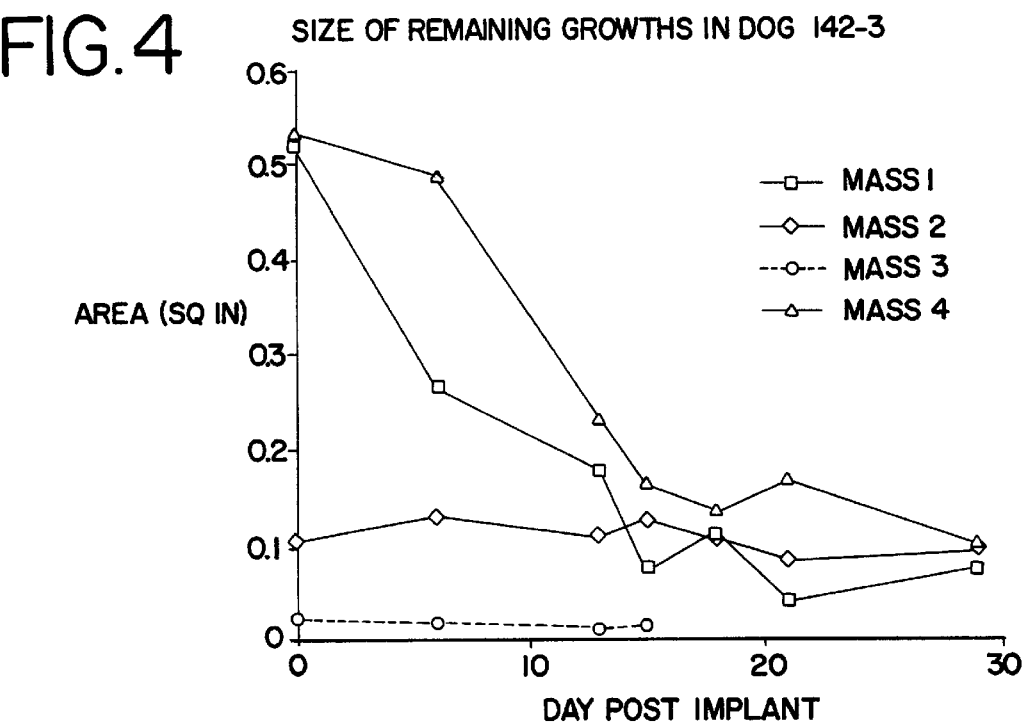
FIG. 4 shows the size of remaining subcutaneous masses in dog 142-3 following implantation of devices containing tissue from one excised mass as described in Example 2.

Following excision of the largest mass from dog 142-3 and insertion of the devices containing tissue from the excised mass, two of the four remaining growths showed a dramatic decrease in size (FIG. 4) as determined by two independent measurements. The other two, which were morphologically distinct, showed no change in size. This decrease in size in the remaining masses occurred without any additional manipulation of the animal.

Figure 5:
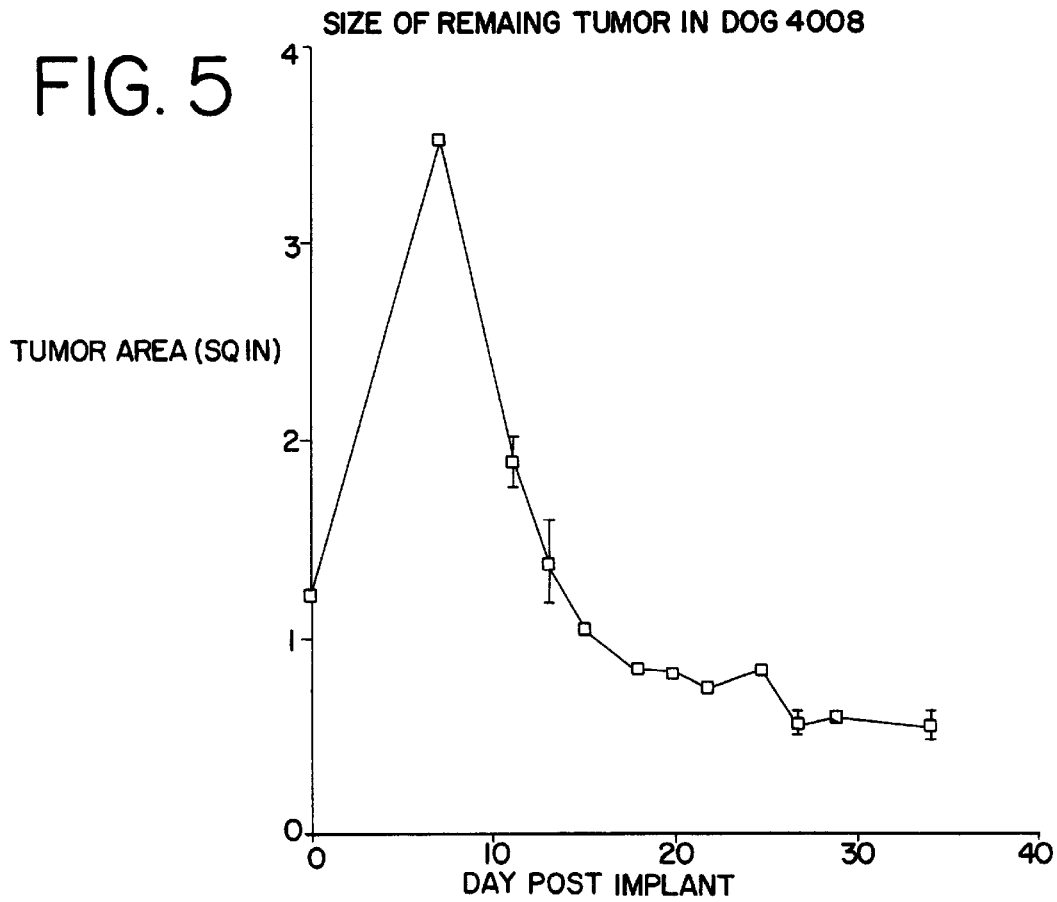
FIG. 5 illustrates the size of the remaining tumor mass in dog 4008 following surgical excision of >95% of the tumor. Excised tumor was used as source of tissue to load devices which were implanted subcutaneously, as described in Example 2.

The size of the remaining tumor in dog 4008 appeared to increase initially but this was probably due to edema resulting from surgical trauma (note increase at day 7, FIG. 5). Subsequently there has been a steady decrease in the size of the remaining tumor as determined by two sets of independent measurements with some leveling out at >30 days post surgery.

EXAMPLE 3

Small Pre-Existing Tumors

Cell lines used: MCA-38 is a murine colon carcinoma which can be maintained in vivo or in vitro. For in vitro maintenance, the cells were grown in RPMI (Sigma Chemical Company, St. Louis Mo.) supplemented with 1 mM HEPES, 1% non-essential amino acids, 1% L-glutamine, 1% sodium pyruvate, 1% penicillin/streptomycin (Sigma ), 0.1% P-mercaptoethanol and 10% fetal bovine serum (Irvine Scientific, Irvine Calif.). Cells were routinely passaged by trypsinization twice a week.

Animals used: Female C57/B6 (Harlan Sprague Dawley) were used. All animals were maintained according to standard procedures for care and use of laboratory animals.

Immunoisolation Device: These studies utilized sonically sealed 4.5 µl ported devices employing laminated membranes as described in co-pending U.S. patent applications Ser. Nos. 7/735,401 and 7/861,512. Devices were sterilized overnight in 70% ethanol and then the ethanol was removed by three washes in sterile saline (Baxter Scientific Products, Waukegan Ill.)

Implantation of devices: For loading, MCA-38 cells were trypsinized, washed, and pelleted by centrifugation. Except where indicated, $10^6$ MCA-38 cells were encapsulated into 4.5 µl ported devices by loading 3 µl of the pelleted cells into the central lumen of the immunoisolation device using a Hamilton syringe.

Where indicated, cells were exposed to 3500 Rads before loading. Devices were sealed with a silicone plug laid down using a 23 gauge needle and syringe. The device port was completely filled with silicone and the port was cut in half. The remaining port was dipped briefly in 70% ethanol. The loaded devices were washed through three changes of saline. Devices were placed in RPMI 1640 supplemented as described above and incubated at 37° C. until implantation.

The animals receiving implants were anaesthetized by intraperitoneal injection of 0.2–0.3 ml of the mixture of 1 ml ketamine and 0.75 ml rompum diluted into 1 ml of sterile saline. The abdominal area was swabbed with betadine and a ventral midline incision was made. Using a hemostat a small pocket was made on either side of the midline incision and one device was inserted into each pocket. Once the devices were inserted the incision was closed using sterile staples and the abdominal area swabbed again with betadine.

Injection of free irradiated cells: At the time of implant some experimental animals were also given an injection of free irradiated tumor cells. For irradiation the cells were prepared as described above for loading. The cells were suspended at a concentration of $10^6$ cells in 50 ml. The cells received 3500–4000 Rads from a cobalt-60 source. $10^6$ cells were injected.

Tumor challenge: For initiating tumors before implant, animals were injected with $10^3$ free MCA-38 cells 3–7 days before implantation. Injections were made either by intramuscular injection into the right hind leg or into the dorsal subcutaneous space. Preliminary studies have shown that as few as 500 free MCA-38 cells are sufficient for tumor formation. In the case of a second challenge following implant, the second injection was made into the left hind leg.

Figure 6:
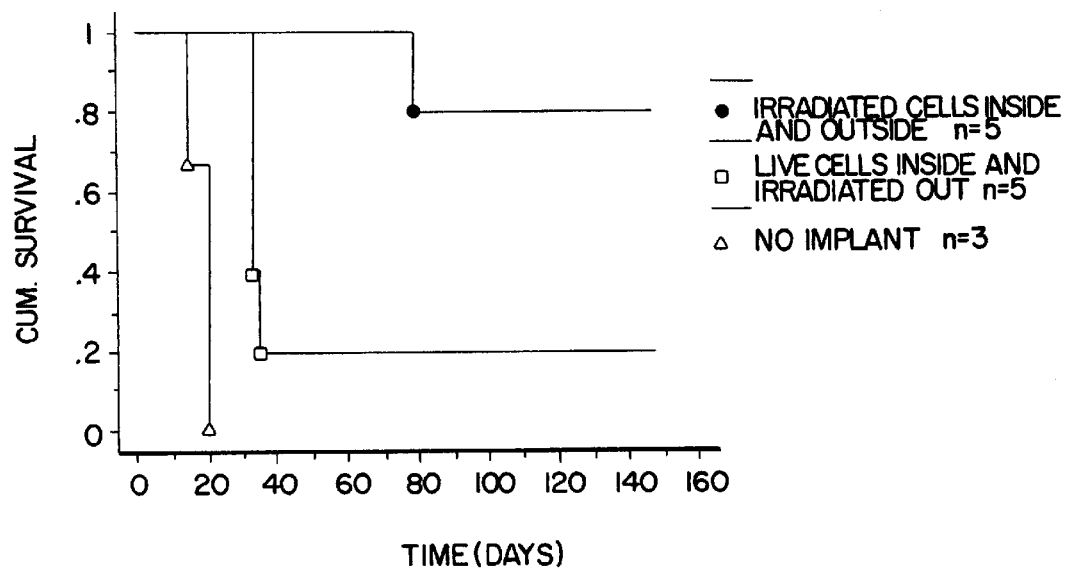
FIG. 6 (from Example 3) shows the survival rate of C57/B6 mice in which preexisting MCA-38 tumor was treated by administration of irradiated MCA-38 tumor cells both inside and outside the chamber. It also shows the survival rate for treatment by administration of unirradiated cells inside the chamber in combination with irradiated cells outside of the chamber.
Figure 7:
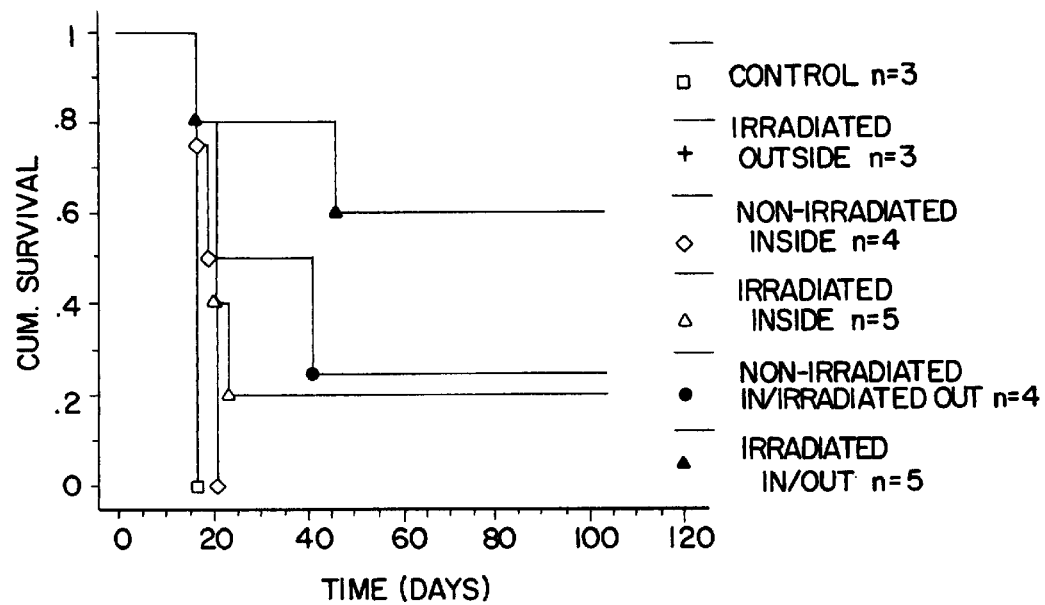
FIG. 7 (from Example 3) shows the survival rate of C57/B6 mice in which preexisting MCA-38 tumor was treated by administration of irradiated and nonirradiated MCA-38 tumor cells both inside and outside of the chamber.

Treatment of pre-existing tumors: Animals were injected with $10^3$ free tumor cells three days before implantation. At time of implant they received two devices containing irradiated MCA-38 cells and were also given an injection of $10^6$ free irradiated tumor cells exterior to the devices. As shown in FIG. 6, none of the five animals treated with irradiated cells both inside and outside of the device developed tumor at in the first 90 days. On day 90 two of these animals were challenged with $10^6$ tumor cells, one of these two animals developed a tumor from this challenge. All of the other animals have remained tumor free for >150 days. As illustrated in FIG. 7, this treatment works best with the combination of irradiated cells in the device and an injection of free irradiated cells outside of the device. Although some protection is afforded by administering unirradiated tumor cells in the device in combination with free irradiated cells, it is less effective than administering irradiated cells in the device in combination with free irradiated cells. Injection of free irradiated cells alone has no effect on tumor development.

Figure 8:
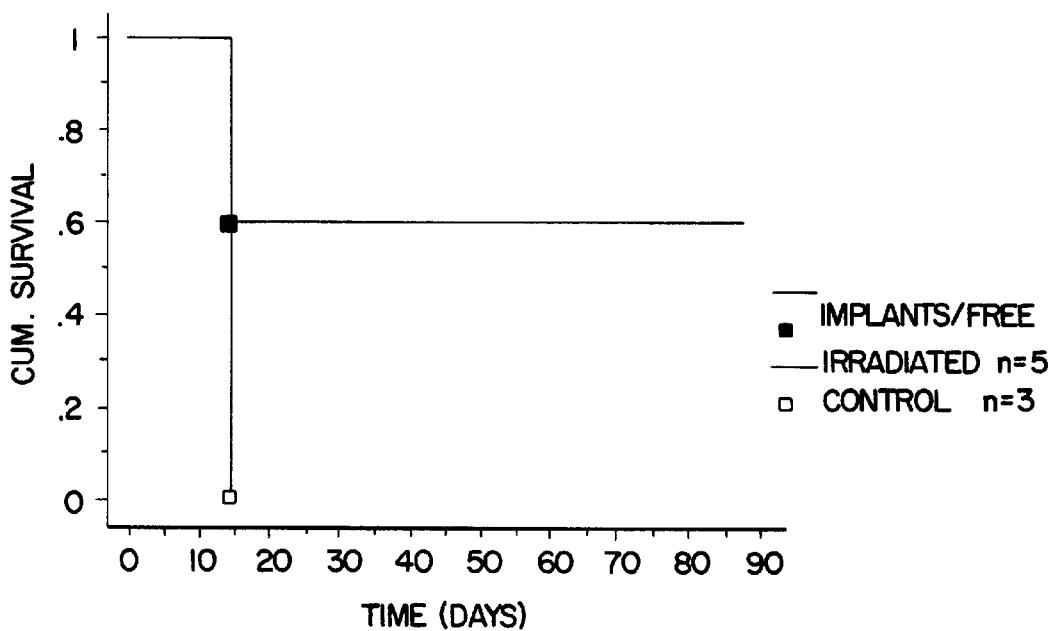
FIG. 8 (from Example 3) shows the survival rate of C57/B6 mice in which preexisting MCA-38 tumor in the dorsal subcutaneous space was treated by administration of irradiated tumor cells both inside and outside of the chamber.

When tumors were initiated in the dorsal subcutaneous space, implantation of devices containing irradiated cells along with an injection of free irradiated cells were able to rescue 60% of the treated animals (all of the untreated animals developed tumor at the site where the original tumors were initiated) (FIG. 8).

EXAMPLE 4

Device Therapy after Tumor Resection

Cell lines used: MCA-38 is a murine colon carcinoma which can be maintained in vivo or in vitro. For in vitro maintenance, the cells were grown in RPMI (Sigma Chemical Company, St. Louis Mo.) supplemented with 1 mM HEPES, 1% non-essential amino acids, 1% L-glutamine, 1% sodium pyruvate, 1% penicillin/streptomycin (Sigma), 0.1% P-mercaptoethanol and 10% fetal bovine serum (Irvine Scientific, Irvine Calif.). Cells were routinely passaged by trypsinization twice a week.

Animals used: Female C57/B6 (Harlan Sprague Dawley) were used. All animals were maintained according to standard procedures for care and use of laboratory animals.

Immunoisolation Device: These studies utilized the sonically sealed 4.5 µl ported devices employing laminated membranes described in co-pending U.S. patent application Ser. Nos. 7/735,401 and 7/861,512. Devices were sterilized overnight in 70% ethanol and then the ethanol was removed by three washes in sterile saline (Baxter Scientific Products, Waukegan Ill.)

Implantation of devices: For loading, MCA-38 cells were trypsinized, washed and pelleted by centrifugation. Except where indicated, $10^6$ MCA-38 cells were encapsulated into 4.5 µl ported devices by loading 3 µl of the pelleted cells into the central lumen of the immunoisolation device using a Hamilton syringe. Devices were sealed with a silicone plug laid down using a 23 gauge needle and syringe. The device port was completely filled with silicone and the port was cut in half. The remaining port was dipped briefly in 70% ethanol. The loaded devices were washed through three changes of saline. Devices were placed in RPMI 1640 supplemented as described above and incubated at 37° C. until implantation.

The animals receiving implants were anaesthetized by intraperitoneal injection of 0.2–0.3 ml of the mixture of 1 ml ketamine and 0.75 ml rompum diluted into 1 ml of sterile saline. The abdominal area was swabbed with betadine and a ventral midline incision was made. Using a hemostat a small pocket was made on either side of the midline incision and one device was inserted into each pocket. Once the devices were inserted the incision was closed using sterile staples and the abdominal area swabbed again with betadine.

Tumor challenge: To initiate tumors, animals were injected with $10^5$ free CA-38 cells 3–7 days before implantation. Injections were made into the dorsal subcutaneous space. Preliminary studies have shown that as few as 500 free MCA-38 cells are sufficient for tumor formation.

Figure 9:
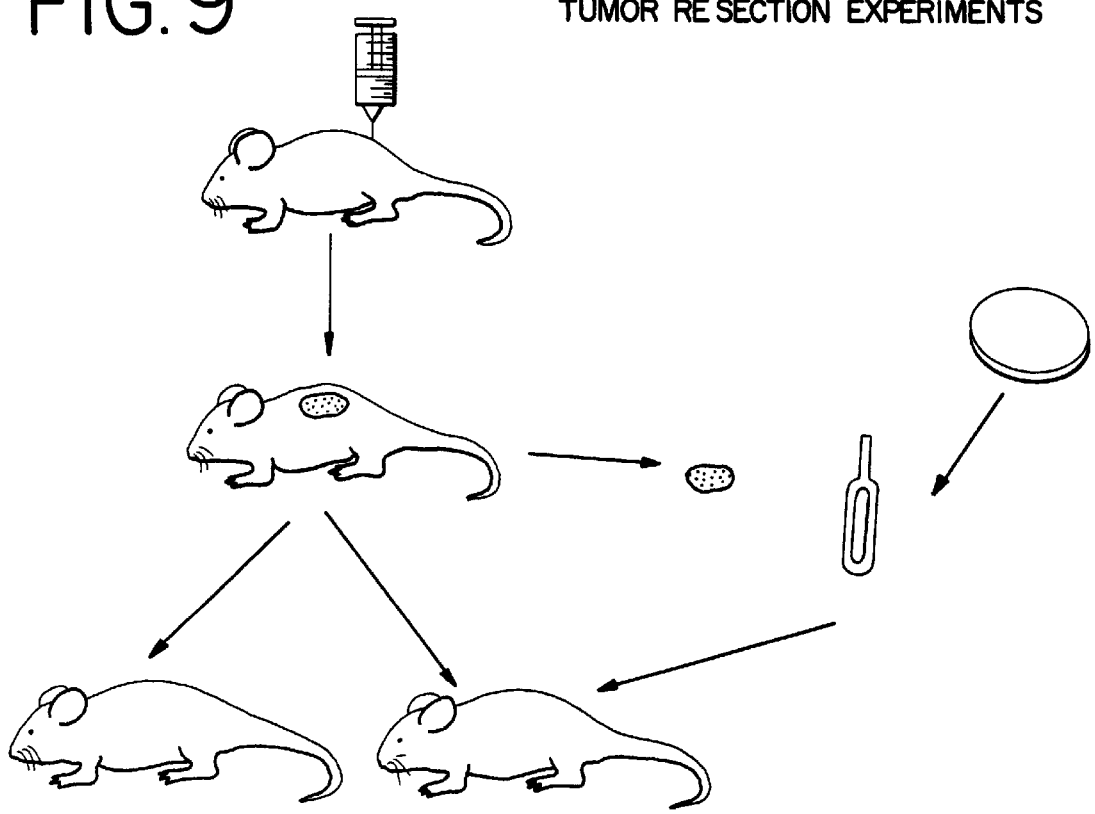
FIG. 9 shows the protocol for an experiment of Example 4.
Figure 10:
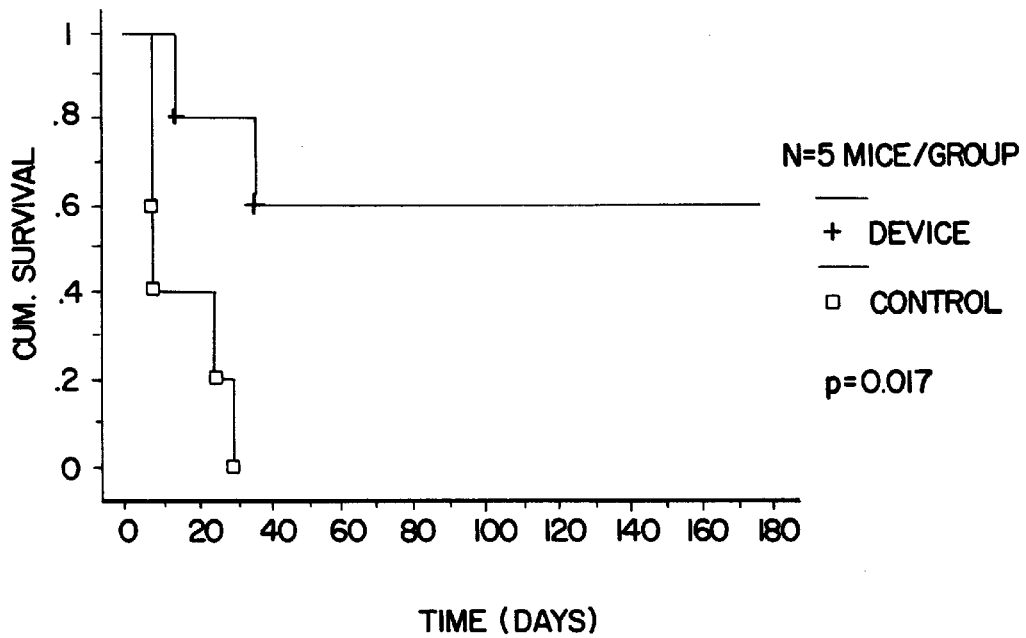
FIG. 10 (from Example 4) shows the survival rate of C57/B6 mice in which preexisting MCA-38 tumor was resected and then treated by administration of chambers containing unirradiated MCA-38 tumor cells and no cells outside the chamber.

Use of immunoisolation devices containing MCA-38 cells as a tumor therapy for treatment following tumor resection: The protocol for this experiment is outlined in FIG. 9. Briefly, animals were injected with $10^5$ cells in the dorsal subcutaneous space and monitored until palpable tumors were observed. On day 10 the tumors were surgically removed from all of the animals. Half of the animals (n=5) received no further treatment. The other half (n=5) were implanted with two devices each containing $10^6$ unirradiated MCA-38 cells. The devices were implanted subcutaneously on the ventral side. Both groups of animals were monitored for redevelopment of tumor at the original tumor site. As shown in FIG. 10, all of the control animals (without implants) redeveloped tumor at the original tumor site within thirty days of the surgery. While two of the animals with implants also redeveloped tumor, three did not and have remained tumor free for >180 days. The differences between these groups are highly significant (p<0.05).

EXAMPLE 5

Rodent Melanoma Model

Cell lines used: B16 is a murine melanoma which can be maintained in vivo or in vitro. For in vitro maintenance, the cells were grown in RPMI (Sigma Chemical Company, St. Louis Mo.) supplemented with 1 mM HEPES, 1% nonessential amino acids, 1% L-glutamine, 1% sodium pyruvate, 1% penicillin/streptomycin (Sigma), 0.1% P-mercaptoethanol and 10% fetal bovine serum (Irvine Scientific, Irvine Calif.). Cells were routinely passaged by trypsinization twice a week.

Animals used: Female C57/B6 were used. All animals were maintained according to standard procedures for care and use of laboratory animals.

Immunoisolation Device: These studies utilized the sonically sealed 4.5 $\mu$l employing laminated membranes described in co-pending U.S. patent application Ser. Nos. 7/735,401 and 7/861,512. Devices were sterilized overnight in 70% ethanol and then the ethanol was removed by three washes in sterile saline (Baxter Scientific Products, Waukegan Ill.).

Implantation of devices: For loading, B16 cells were trypsinized, washed and pelleted by centrifugation. Except where indicated, $10^6$ B16 cells were encapsulated into 4.5 $\mu$l ported devices by loading 3 $\mu$l of the pelleted cells into the central lumen of the immunoisolation device using a Hamilton syringe. Devices were sealed with a silicone plug laid down using a 23 gauge needle and syringe. The device port was completely filled with silicone and the port was cut in halt The remaining port was dipped briefly in 70% ethanol. The loaded devices were washed through three changes of saline. Devices were placed in RPMI 1640 supplemented as described above and incubated at 37° C. until implantation.

The animals receiving implants were anaesthetized by intraperitoneal injection of 0.2–0.3 ml of the mixture of 1 ml ketamine and 0.75 ml rompum diluted into 1 ml of sterile saline. The abdominal area was swabbed with betadine and a ventral midline incision was made. Using a hemostat a small pocket was made on either side of the midline incision and one device was inserted into each pocket. Once the devices were inserted the incision was closed using sterile staples and the abdominal area swabbed again with betadine.

Injection of free irradiated cells: At the time of implant all animals with implanted devices were also given an injection of $10^6$ free irradiated cultured B16 cells at the site of the challenge. For irradiation the cells were prepared as described above for loading. The cells were suspended at a concentration of $10^6$ cells in 50 ml. The cells received 3500–4000 Rads from a cobalt-60 source.

Tumor challenge: Four weeks after the implantation of devices, animals were challenged with an injection of unirradiated B16 cells. For challenge $5\times10^5$ freshly trypsinized B16 cells were diluted in 50 $\mu$l of sterile saline and injected into the muscle of the right hind leg. Preliminary studies have shown that $10^4$ free B16 cells are sufficient for tumor formation.

Figure 11:
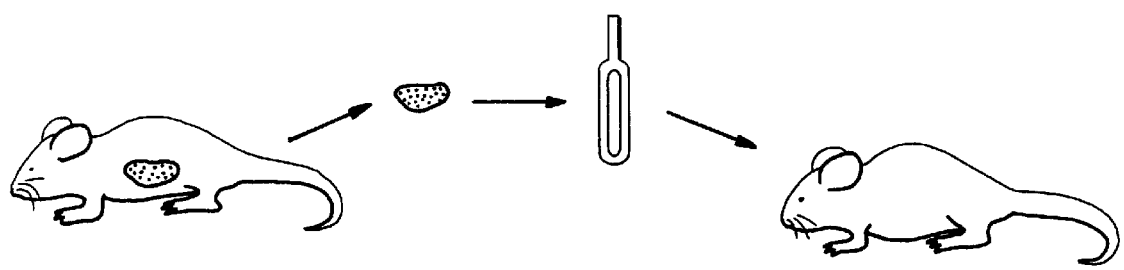
FIG. 11 shows the protocol for the experiment of Example 5.
Figure 12:
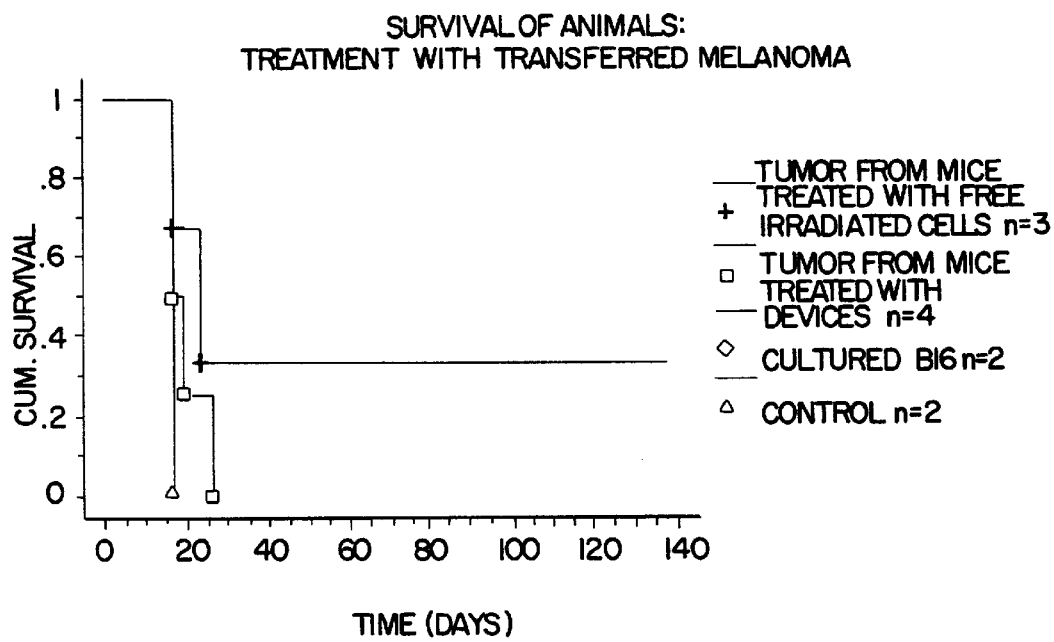
FIG. 12 (from Example 5) shows the survival rate of C57/B6 mice challenged with B16 melanoma after first being immunized with B16 melanoma grown up in and transferred from syngeneic animals.

Use of immunoisolation devices containing in vivo derived tumor tissue as a tumor vaccine: The protocol for this experiment is outlined in FIG. 11, briefly, animals were treated in a first round with either devices containing unirradiated B16 cells or by injection of free, irradiated B16 cells. All of these animals developed tumor after challenge with $5\times10^4$ B16 cells. The tumors from both groups of animals were surgically excised, chopped up into approximately 1 mm$^2$ pieces and loaded into 4.5 $\mu$l devices. A third set of devices was also prepared containing cultured unirradiated B16 cells. These three sets of devices were implanted into a second set of naive animals and all three groups also received an injection of free, irradiated cultured B16 cells; control animals received no treatment. The animals were challenged with cultured B16 cells four weeks later. As shown in FIG. 12, one of three animals immunized with devices containing tumor grown up in animals treated only by injection of free irradiated cells remained tumor free for >140 days after challenge. Thus, the tumor cells used to immunized the naive animals were not cultured cells but rather they were cells subject to evolution while growing up in the first round of animals. These data indicate that chambers containing tumor cells which have been subject to evolution, such as autologus human tumor cells, are likely to be useful in practicing applicants' invention.

EXAMPLE 6

Rodent Ovarian Tumor

Cell lines used: C57ov is a murine tumor which can be maintained in vivo or in vitro. It was identified in the laboratory in an animal given an I.V. injection of B16 cells ($5\times10^5$). Histological examination suggests that it was not B16 derived. For in vitro maintenance, the cells were grown in RPMI (Sigma Chemical Company, St. Louis Mo.) supplemented with 1 mM HEPES, 1% non-essential amino acids, 1% L-glutamine, 1% sodium pyruvate, 1% penicillin/streptomycin (Sigma), 0.1% P-mercaptoethanol and 10% fetal bovine serum (Irvine Scientific, Irvine Calif.). Cells were routinely passaged by trypsinization twice a week.

Animals used: Female C57/B6 were used. All animals were maintained according to standard procedures for care and use of laboratory animals.

Immunoisolation Device: These studies utilized the sonically sealed 4.5 $\mu$l employing laminated membranes described in co-pending U.S. patent application Ser. Nos. 7/735,401 and 7/861,512. Devices were sterilized overnight in 70% ethanol and then the ethanol was removed by three washes in sterile saline (Baxter Scientific Products, Waukegan Ill.).

Implantation of devices: For loading, C57ov cells were trypsinized, washed and pelleted by centrifugation. Except where indicated, $10^6$ C57ov cells were encapsulated into 4.5 $\mu$l ported devices by loading 3 $\mu$l of the pelleted cells into the central lumen of the immunoisolation device using a Hamilton syringe. Devices were sealed with a silicone plug laid down using a 23 gauge needle and syringe. The device port was completely filled with silicone and the port was cut in half. The remaining port was dipped briefly in 70% ethanol.

The loaded devices were washed through three changes of saline. Devices were placed in RPMI 1640 supplemented as described above and incubated at 37° C. until implantation.

The animals receiving implants were anaesthetized by intraperitoneal injection of 0.2–0.3 ml of the mixture of 1 ml ketamine and 0.75 ml rompum diluted into 1 ml of sterile saline. The abdominal area was swabbed with betadine and a ventral midline incision was made. Using a hemostat a small pocket was made on either side of the midline incision and one device was inserted into each pocket. Once the devices were inserted the incision was closed using sterile staples and the abdominal area swabbed again with betadine.

Injection of free irradiated cells: At the time of implant all animals with implanted devices were also given an injection of $10^6$ free irradiated cultured C57ov cells at the site of the challenge. For irradiation the cells were prepared as described above for loading. The cells were suspended at a concentration of $10^6$ cells in 50 μl. The cells received 3500–4000 Rads from a cobalt-60 source.

Tumor challenge: Four weeks after the implantation of devices, animals were challenged with an injection of unirradiated C57ov cells. For challenge $5 \times 10^4$ freshly trypsinized C57ov cells were diluted in 50 μl of sterile saline and injected into the muscle of the right hind leg. Preliminary studies have shown that $10^3$ free C57ov cells are sufficient for tumor formation.

Figure 13:
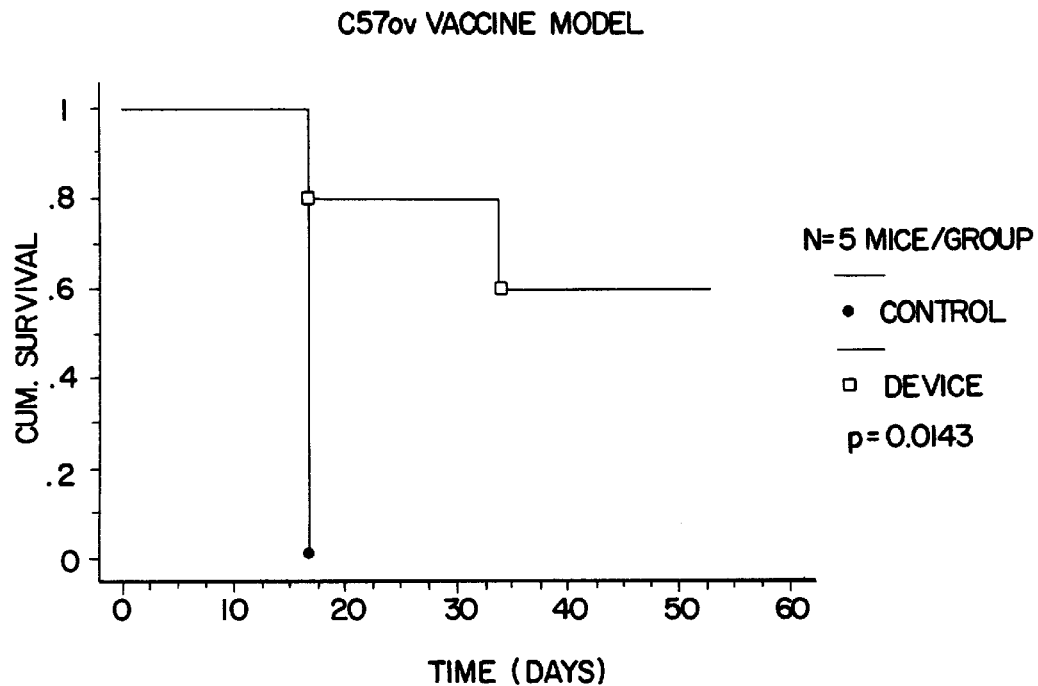
FIG. 13 (from Example 6) shows the survival rate of C57/B6 mice challenged with C57 ovarian tumor four weeks after first being immunized with both free irradiated C57 ovarian tumor cells and devices containing irradiated C57 ovarian tumor.

Use of immunoisolation devices containing C57ov as a tumor vaccine: Animals were implanted with two devices each containing $10^6$ irradiated C57ov cells. At the time of implantation the animals also revieved an injection of $10^6$ irradiated C57ov cells. The animals were challenged with C57ov four weeks later. The results are shown in FIG. 13, 60% of the animals have remained tumor free for >30 days.

While the present invention has been described in terms of specific methods and devices, it is understood that variations and modifications will occur to those skilled in the art upon consideration of the present invention.

Numerous modifications and variations in the invention as described in the above illustrative examples are expected to occur to those skilled in the art and consequently only such limitations as appear in the appended claims are to be placed thereon. Accordingly, it is intended in the appended claims to cover all such equivalent variations which come within the scope of the invention as claimed.

We claim:

1. A method for preventing or suppressing tumor growth in a mammal by administering first tumor cells comprising:
   (a) providing an implantable chamber and first tumor cells contained in the chamber; and
   (b) implanting the chamber containing the first tumor cells into the mammal, wherein the chamber comprises wall means including an interior surface defining the chamber for holding the tumor cells and an exterior surface defining an interface with the mammalian tissue, the interior surface sufficient to isolate the tumor cells from the cellular immune response of the host tissue, the exterior surface having a conformation which allows growth of vascular structures by the mammalian tissue close to but not substantially into the interface and having a nominal pore size ranging from about 0.6 to 20 microns; wherein the first tumor cells have at least one antigen corresponding to an antigen of the mammal's tumor cells and elicit an immune response by the mammal; and wherein the tumor growth is prevented or suppressed.

2. The method of claim 1 further comprising:
   (a) administering a second set of tumor cells which have been rendered nontumorigenic, wherein said second tumor cells are administered to the mammal without containing them in a chamber;
   (b) wherein said second tumor cells have at least one antigen corresponding to an antigen of the mammal's tumor cells.

3. The method of claim 1 wherein the first tumor cells are autologous.

4. The method of claim 2 wherein the first tumor cells and the second tumor cells are autologous.

5. The method of claim 1 wherein at least some of the first tumor cells are proliferative at the time of administration.

6. The method of claim 1 wherein at least some of the first tumor cells are proliferative at the time of administration and at least some of them are proliferative at least 30 days following administration.

7. The method of claim 1 wherein the first tumor cells are not proliferative at the time of administration.

8. The method of claims 1 or 2 further comprising administering a source of cytokine molecules.

9. The method of claim 8 wherein said cytokine molecules are selected from the group consisting of GM-CSF, IL-1, IL-2, IL-3, IL-4, IL-6, IL-10, IL-12, IFN-g, TNF, and TGF-b.

10. The method of claim 8 wherein said source is liposomes containing cytokine molecules.

11. The method of claim 8 wherein said source is microcapsules containing cytokine molecules.

12. The method of claim 8 wherein said source is somatic cells engineered to express and secrete cytokine molecules, where the somatic cells are also contained in the chamber.

13. The method of claim 8 wherein said source is at least some of said first tumor cells engineered to express and secrete cytokine molecules.

14. The method of claim 2 wherein said second tumor cells are engineered to express and secrete cytokine molecules.

15. The method of claims 1 or 2 wherein the chamber is selected from the group consisting of microcapsules, hollow fibers, ultrafiltration membrane chambers, membrane diffusion chambers, and vascular perfusion devices.

16. The method of claims 1 or 2 wherein said chamber includes a port means for providing access to the chamber.

17. The method of claims 1 or 2 wherein said cancer is a solid tumor, metastatic tumor or leukemic cancer.

18. The method of claims 1 or 2 where the cancer is lymphoma, melanoma, colon carcinoma, mammary carcinoma, lung carcinoma, fibrosarcoma, renal carcinoma, neuroblastoma, or ovarian carcinoma.

19. A method for preventing or suppressing tumor growth in a mammal by administering first tumor cells comprising:
   (a) providing an implantable chamber and first tumor cells contained in the chamber; and
   (b) implanting the chamber containing the first tumor cells into the mammal, wherein the chamber comprises wall means including an interior surface defining the chamber for holding the tumor cells and an exterior surface defining an interface with the mammalian tissue, the interior surface sufficient to isolate the tumor cells from the cellular immune response of the host tissue, the exterior surface having a conformation which allows growth of vascular structures by the mammalian tissue close to but not substantially into the interface and having a nominal pore size ranging from about 0.6 to 20 microns and wherein the first tumor cells are allogeneic to the mammal, have at least one antigen corresponding to an antigen of the mammal's tumor cells, and elicit an immune response by the mammal; and wherein the tumor growth is prevented or suppressed.

20. The method of claim 19 further comprising:
(a) administering a second set of tumor cells which have been rendered nontumorigenic, wherein said second tumor cells are administered to the mammal without containing them in the chamber;
(b) wherein said second tumor cells have at least one tumor antigen corresponding to an antigen of the mammal's tumor cells.

21. The method of claim 20 wherein the first tumor cells and the second tumor cells are allogeneic.

22. The method of claim 20 wherein the first tumor cells are from an allogeneic tumor cell line.

23. The method of claim 20 wherein the first tumor cells and the second tumor cells are from allogeneic tumor cell lines.

24. The method of claim 19 wherein at least some of the first tumor cells are proliferative at the time of administration.

25. The method of claim 19 wherein at least some of the first tumor cells are proliferative at the time of administration and at least some of them are proliferative at least 30 days following administration.

26. The method of claim 19 wherein the first tumor cells are not proliferative at the time of administration.

27. The method of claims 19 or 20 further comprising administering a source of cytokine molecules.

28. The method of claim 27 wherein said cytokine molecules are selected from the group consisting of GM-CSF, IL-1, IL-2, IL-3, IL-4, IL-6, IL-10, IL-12, IFN-g, TNF, and TGF-b.

29. The method of claim 27 wherein said source is liposomes containing cytokine molecules.

30. The method of claim 27 wherein said source is microcapsules containing cytokine molecules.

31. The method of claim 27 wherein said source is somatic cells engineered to express and secrete cytokine molecules, where the somatic cells are also contained in the chamber.

32. The method of claim 27 wherein said source is at least some of said first tumor cells engineered to express and secrete immunopotentiating molecules.

33. The method of claim 20 wherein said second tumor cells are engineered to express and secrete cytokine molecules.

34. The method of claims 19 or 20 wherein the chamber is selected from the group consisting of microcapsules, hollow fibers, ultrafiltration membrane chambers, membrane diffusion chambers, and vascular perfusion devices.

35. The method of claims 19 or 20 wherein said chamber includes a port means for providing access to the chamber.

36. The method of claims 19 or 20 wherein said cancer is a solid tumor, metastatic tumor or leukemic cancer.

37. The method of claims 19 or 20 where the cancer is lymphoma, melanoma, colon carcinoma, mammary carcinoma, lung carcinoma, fibrosarcoma, renal carcinoma, neuroblastoma, or ovarian carcinoma.

38. The method of claim 1, wherein the wall means includes a port member for providing access to the chamber.

39. The method of claim 19, wherein the wall means includes a port member for providing access to the chamber.

* * * * *